(12) United States Patent
Truckai et al.

(10) Patent No.: US 8,556,910 B2
(45) Date of Patent: Oct. 15, 2013

(54) BONE TREATMENT SYSTEMS AND METHODS

(75) Inventors: Csaba Truckai, Saratoga, CA (US);
Robert Luzzi, Pleasanton, CA (US);
John H. Shadduck, Tiburon, CA (US)

(73) Assignee: Dfine, Inc., San Jose, CA (US)

( * ) Notice: Subject to any disclaimer, the term of this patent is extended or adjusted under 35 U.S.C. 154(b) by 1203 days.

(21) Appl. No.: 12/062,345

(22) Filed: Apr. 3, 2008

(65) Prior Publication Data
US 2008/0255570 A1 Oct. 16, 2008

Related U.S. Application Data

(60) Provisional application No. 60/907,467, filed on Apr. 3, 2007, provisional application No. 60/907,468, filed on Apr. 3, 2007, provisional application No. 60/907,469, filed on Apr. 3, 2007, provisional application No. 60/929,416, filed on Jun. 26, 2007.

(51) Int. Cl.
*A61B 17/58* (2006.01)
*A61B 17/60* (2006.01)
*A61F 2/00* (2006.01)

(52) U.S. Cl.
USPC .......................................................... 606/94

(58) Field of Classification Search
USPC .................................................... 606/92–94
See application file for complete search history.

(56) References Cited

U.S. PATENT DOCUMENTS

| | | | |
|---|---|---|---|
| 3,349,840 A | 10/1967 | Tope et al. | |
| 4,250,887 A | 2/1981 | Dardik et al. | |
| 4,265,618 A | 5/1981 | Herskovitz et al. | |
| 4,294,251 A | 10/1981 | Grennwald et al. | |
| 4,338,925 A | 7/1982 | Miller | |
| 4,377,168 A | 3/1983 | Rzasa et al. | |

(Continued)

FOREIGN PATENT DOCUMENTS

| | | |
|---|---|---|
| JP | 2009-504363 | 2/2009 |
| WO | WO 02/058592 | 8/2002 |

(Continued)

OTHER PUBLICATIONS

International Search Report and Written Opinion, mailing date Sep. 11, 2008, PCT/US08/59305.

(Continued)

*Primary Examiner* — Sameh Boles
(74) *Attorney, Agent, or Firm* — Knobbe Martens Olson & Bear LLP

(57) ABSTRACT

Systems and methods for delivering bone cement into a bone can include a handle body defining a flow path, a thermal emitter in the handle body to apply energy to bone cement passing through the flow path, a source of bone cement and an injection cannula. The cannula can be in communication with the flow path such that inserting the cannula into a bone can allow a flow of bone cement therethrough to an opening at a distal end of the cannula. Other systems and methods for delivering bone cement into a bone can include an injector body with a handle portion, and a cannula, a bone cement container, a low pressure drive mechanism configured to effect a flow of bone cement from said container to the injector body and a high pressure drive mechanism configured to effect a flow of bone cement through the injector body into the bone.

29 Claims, 16 Drawing Sheets

(56) References Cited

U.S. PATENT DOCUMENTS

| | | |
|---|---|---|
| 4,735,625 A | 4/1988 | Davidson |
| 4,772,287 A | 9/1988 | Ray et al. |
| 4,815,454 A | 3/1989 | Dozier |
| 4,963,151 A | 10/1990 | Ducheyne et al. |
| 4,969,888 A | 11/1990 | Scholten et al. |
| 4,969,906 A | 11/1990 | Kronman |
| 5,037,437 A | 8/1991 | Matsen |
| 5,108,404 A | 4/1992 | Scholten |
| 5,130,950 A | 7/1992 | Orban et al. |
| 5,145,250 A | 9/1992 | Planck et al. |
| 5,324,305 A * | 6/1994 | Kanner .................. 606/213 |
| 5,431,654 A | 7/1995 | Nic |
| 5,514,135 A | 5/1996 | Earle |
| 5,542,928 A | 8/1996 | Evans et al. |
| 5,679,299 A | 10/1997 | Gilbert et al. |
| 5,693,099 A | 12/1997 | Harle |
| 5,788,711 A | 8/1998 | Lehner et al. |
| 5,814,681 A | 9/1998 | Hino et al. |
| 5,954,716 A | 9/1999 | Sharkey et al. |
| 6,048,346 A | 4/2000 | Reiley et al. |
| 6,075,067 A | 6/2000 | Lidgren |
| 6,077,256 A | 6/2000 | Mann |
| 6,122,549 A | 9/2000 | Sharkey et al. |
| 6,171,312 B1 | 1/2001 | Beaty |
| 6,228,072 B1 | 5/2001 | Omaleki et al. |
| 6,231,615 B1 | 5/2001 | Preissman |
| 6,235,043 B1 | 5/2001 | Reiley et al. |
| 6,236,020 B1 | 5/2001 | Friedman |
| 6,241,734 B1 | 6/2001 | Scribner |
| 6,248,110 B1 | 6/2001 | Reiley et al. |
| 6,261,289 B1 | 7/2001 | Levy |
| 6,264,659 B1 * | 7/2001 | Ross et al. .................. 606/93 |
| 6,280,456 B1 | 8/2001 | Scribner et al. |
| 6,284,809 B1 | 9/2001 | Plummer et al. |
| 6,309,420 B1 | 10/2001 | Preissman |
| 6,312,254 B1 | 11/2001 | Friedman |
| 6,316,885 B1 | 11/2001 | Collins et al. |
| 6,319,255 B1 | 11/2001 | Grundei et al. |
| 6,332,894 B1 | 12/2001 | Stalcup et al. |
| 6,348,055 B1 | 2/2002 | Preissman |
| 6,358,254 B1 | 3/2002 | Anderson |
| 6,383,190 B1 | 5/2002 | Preissman |
| 6,425,923 B1 | 7/2002 | Stalcup et al. |
| 6,436,143 B1 | 8/2002 | Ross et al. |
| 6,439,439 B1 | 8/2002 | Rickard |
| 6,440,138 B1 | 8/2002 | Reiley et al. |
| 6,443,988 B2 | 9/2002 | Felt et al. |
| 6,447,514 B1 | 9/2002 | Stalcup et al. |
| 6,485,436 B1 | 11/2002 | Truckai |
| 6,524,102 B2 | 2/2003 | Davis |
| 6,575,331 B1 | 6/2003 | Peeler et al. |
| 6,610,079 B1 | 8/2003 | Li et al. |
| 6,613,054 B2 | 9/2003 | Scribner et al. |
| 6,632,235 B2 | 10/2003 | Weikel et al. |
| 6,662,969 B2 | 12/2003 | Peeler et al. |
| 6,676,664 B1 | 1/2004 | Al-Assir |
| 6,706,069 B2 | 3/2004 | Berger |
| 6,712,852 B1 | 3/2004 | Chung et al. |
| 6,716,216 B1 | 4/2004 | Boucher et al. |
| 6,719,773 B1 | 4/2004 | Boucher et al. |
| 6,723,095 B2 | 4/2004 | Hammerslag |
| 6,726,691 B2 | 4/2004 | Osorio et al. |
| 6,736,537 B2 | 5/2004 | Coffeen et al. |
| 6,740,093 B2 | 5/2004 | Hochschuler et al. |
| 6,767,936 B2 | 7/2004 | Walz et al. |
| 6,783,515 B1 | 8/2004 | Miller |
| 6,814,736 B2 | 11/2004 | Reiley et al. |
| 6,863,672 B2 | 3/2005 | Reiley et al. |
| 6,899,713 B2 | 5/2005 | Shaolian et al. |
| 6,923,813 B2 | 8/2005 | Phillips |
| 6,929,640 B1 | 8/2005 | Underwood |
| 6,957,747 B2 | 10/2005 | Peeler et al. |
| 6,958,061 B2 | 10/2005 | Truckai et al. |
| 6,964,667 B2 | 11/2005 | Shaolian et al. |
| 6,979,352 B2 | 12/2005 | Reynolds |
| 6,985,061 B2 | 1/2006 | Hafskjold et al. |
| 7,008,433 B2 | 3/2006 | Voellmicke et al. |
| 7,044,954 B2 | 5/2006 | Reiley |
| 7,048,743 B2 | 5/2006 | Miller et al. |
| 7,081,125 B2 | 7/2006 | Edwards et al. |
| 7,108,696 B2 | 9/2006 | Daniel et al. |
| 7,112,205 B2 | 9/2006 | Carrison |
| 7,115,163 B2 | 10/2006 | Zimmermann |
| 7,153,306 B2 | 12/2006 | Ralph et al. |
| 7,153,307 B2 | 12/2006 | Scribner et al. |
| 7,156,861 B2 | 1/2007 | Scribner et al. |
| 7,160,020 B2 | 1/2007 | Sand |
| 7,166,121 B2 | 1/2007 | Reiley et al. |
| 7,273,523 B2 | 9/2007 | Wenz |
| 7,399,306 B2 | 7/2008 | Reiley et al. |
| 7,559,932 B2 | 7/2009 | Truckai et al. |
| 7,572,263 B2 | 8/2009 | Preissman |
| 7,662,133 B2 | 2/2010 | Scarborough et al. |
| 7,678,116 B2 | 3/2010 | Truckai et al. |
| 8,109,933 B2 | 2/2012 | Truckai et al. |
| 2001/0011190 A1 | 8/2001 | Park |
| 2002/0026195 A1 | 2/2002 | Layne et al. |
| 2002/0068974 A1 | 6/2002 | Kuslich et al. |
| 2002/0082608 A1 | 6/2002 | Reiley et al. |
| 2002/0099385 A1 | 7/2002 | Ralph et al. |
| 2002/0147497 A1 | 10/2002 | Belef et al. |
| 2002/0156483 A1 | 10/2002 | Voellmicke et al. |
| 2002/0161373 A1 | 10/2002 | Osorio et al. |
| 2003/0032733 A1 | 2/2003 | Fisher et al. |
| 2003/0032929 A1 | 2/2003 | McGuckin |
| 2003/0130373 A1 | 7/2003 | Walz et al. |
| 2003/0130664 A1 | 7/2003 | Boucher et al. |
| 2003/0130738 A1 | 7/2003 | Hovda et al. |
| 2003/0195547 A1 | 10/2003 | Scribner et al. |
| 2003/0220648 A1 | 11/2003 | Osorio et al. |
| 2003/0233096 A1 | 12/2003 | Osorio et al. |
| 2004/0002692 A1 | 1/2004 | Claude et al. |
| 2004/0006347 A1 | 1/2004 | Sproul |
| 2004/0024410 A1 | 2/2004 | Olson |
| 2004/0073308 A1 | 4/2004 | Kuslich et al. |
| 2004/0083002 A1 | 4/2004 | Belef et al. |
| 2004/0092892 A1 | 5/2004 | Kagen et al. |
| 2004/0092948 A1 | 5/2004 | Stevens et al. |
| 2004/0102845 A1 | 5/2004 | Reynolds |
| 2004/0110285 A1 | 6/2004 | Lendlein |
| 2004/0127475 A1 | 7/2004 | New et al. |
| 2004/0138748 A1 | 7/2004 | Boyer, II et al. |
| 2004/0167561 A1 | 8/2004 | Boucher et al. |
| 2004/0172132 A1 | 9/2004 | Ginn |
| 2004/0186576 A1 | 9/2004 | Biscup et al. |
| 2004/0193171 A1 | 9/2004 | DiMauro et al. |
| 2004/0210231 A1 | 10/2004 | Broucher et al. |
| 2004/0215202 A1 | 10/2004 | Preissman |
| 2004/0225296 A1 | 11/2004 | Reiss et al. |
| 2004/0225926 A1 | 11/2004 | Scales |
| 2004/0228898 A1 | 11/2004 | Ross et al. |
| 2004/0267271 A9 | 12/2004 | Scribner et al. |
| 2004/0267272 A1 | 12/2004 | Henniges |
| 2005/0010231 A1 | 1/2005 | Myers |
| 2005/0015148 A1 | 1/2005 | Jansen et al. |
| 2005/0059979 A1 | 3/2005 | Yetkinler |
| 2005/0070915 A1 | 3/2005 | Mazzuca et al. |
| 2005/0113843 A1 | 5/2005 | Arramon |
| 2005/0180806 A1 | 8/2005 | Green et al. |
| 2005/0209595 A1 | 9/2005 | Karmon |
| 2005/0222681 A1 | 10/2005 | Richley et al. |
| 2005/0245938 A1 | 11/2005 | Kochan |
| 2005/0251149 A1 | 11/2005 | Wenz |
| 2006/0052743 A1 | 3/2006 | Reynolds |
| 2006/0052794 A1 | 3/2006 | McGill et al. |
| 2006/0052873 A1 | 3/2006 | Buck et al. |
| 2006/0074433 A1 | 4/2006 | McGill et al. |
| 2006/0079905 A1 | 4/2006 | Beyar et al. |
| 2006/0100635 A1 | 5/2006 | Reiley et al. |
| 2006/0122614 A1 | 6/2006 | Truckai et al. |
| 2006/0122621 A1 * | 6/2006 | Truckai et al. .................. 606/93 |
| 2006/0122622 A1 | 6/2006 | Truckai et al. |
| 2006/0122623 A1 | 6/2006 | Truckai et al. |
| 2006/0122624 A1 | 6/2006 | Truckai et al. |

(56) References Cited

U.S. PATENT DOCUMENTS

| | | |
|---|---|---|
| 2006/0122625 A1 | 6/2006 | Truckai et al. |
| 2006/0150862 A1 | 7/2006 | Zhao et al. |
| 2006/0182780 A1 | 8/2006 | Riley et al. |
| 2006/0264965 A1 | 11/2006 | Shadduck et al. |
| 2006/0264967 A1 | 11/2006 | Ferreyro et al. |
| 2007/0022912 A1 | 2/2007 | Zimmerman |
| 2007/0027230 A1 | 2/2007 | Beyar et al. |
| 2007/0042016 A1 | 2/2007 | Nayak et al. |
| 2007/0112299 A1 | 5/2007 | Smit et al. |
| 2007/0118144 A1 | 5/2007 | Truckai et al. |
| 2007/0162043 A1 | 7/2007 | Truckai et al. |
| 2007/0191858 A1 | 8/2007 | Truckai et al. |
| 2007/0191964 A1 | 8/2007 | Preissman |
| 2007/0198023 A1 | 8/2007 | Sand et al. |
| 2007/0233148 A1 | 10/2007 | Truckai et al. |
| 2007/0282346 A1 | 12/2007 | Scribner et al. |
| 2008/0103505 A1 | 5/2008 | Fransen |
| 2008/0195112 A1 | 8/2008 | Liu et al. |
| 2008/0195114 A1 | 8/2008 | Murphy |
| 2008/0249530 A1 | 10/2008 | Truckai et al. |
| 2009/0024161 A1 | 1/2009 | Bonutti et al. |

FOREIGN PATENT DOCUMENTS

| | | |
|---|---|---|
| WO | WO 02/064062 | 8/2002 |
| WO | WO 02/087416 | 11/2002 |
| WO | WO 2004/075954 | 9/2004 |
| WO | WO 2006/031490 | 3/2006 |
| WO | WO 2006/062916 | 6/2006 |
| WO | WO 2006/130491 A | 12/2006 |
| WO | WO 2007-024641 | 3/2007 |
| WO | WO 2007/028120 | 3/2007 |

OTHER PUBLICATIONS

Office Action in U.S. Appl. No. 11/165,652 mailed Sep. 19, 2008.
Office Action in U.S. Appl. No. 11/165,651 mailed Sep. 22, 2008.
Office Action in U.S. Appl. No. 11/196,045 mailed Oct. 3, 2008.
Office Action in U.S. Appl. No. 11/196,089 mailed Sep. 19, 2008.
Office Action in U.S. Appl. No. 11/208,448 mailed Sep. 8, 2008.
Office Action in U.S. Appl. No. 11/209,035 mailed Sep. 18, 2008.
Carrodeguas, et al., "Injectable Acrylic Bone Cements for Vertebroplasty with Improved Properties", Journal of Biomedical Materials Research, XP002312783, vol. 68, No. 1, Jan. 15, 2004, pp. 94-104.
Furderer S, Anders M, Schwindling B, Salick M, Duber C, Wenda K, Urban R, Gluck M, Eysel P., "Vertebral body stenting. A method for repositioning and augmenting vertebral compression fractures", Orthopade. Apr. 2002; 31(4):356-61, Abstract.
International Search Report, mailing date May 31, 2006, PCT/US2005/044055, 4 pg.
Office Action in U.S. Appl. No. 11/165,045, mailed Mar. 26, 2008.
Office Action in U.S. Appl. No. 11/165,651, mailed Sep. 21, 2007.
Office Action in U.S. Appl. No. 11/165,651, mailed Mar. 24, 2008.
Office Action in U.S. Appl. No. 11/165,652, mailed Oct. 3, 2007.
Office Action in U.S. Appl. No. 11/165,652, mailed Mar. 20, 2008.
Office Action in U.S. Appl. No. 11/166,045, mailed Mar. 26, 2008.
Office Action in U.S. Appl. No. 11/196,089, mailed Jan. 3, 2008.
Office Action in U.S. Appl. No. 11/208,448, mailed Nov. 30, 2007.
Office Action in U.S. Appl. No. 11/209,035, mailed Jan. 30, 2008.
Office Action in U.S. Appl. No. 12/062,337, dated Sep. 26, 2011.

* cited by examiner

BONE TREATMENT SYSTEMS AND METHODS

CROSS-REFERENCE TO RELATED APPLICATIONS

This application claims the benefit of the following U.S. Provisional Applications: App. No. 60/907,467 filed Apr. 3, 2007; App. No. 60/907,468 filed Apr. 3, 2007; App. No. 60/907,469 filed Apr. 3, 2007; and App. No. 60/929,416 filed Jun. 26, 2007; the entire contents of which are hereby incorporated by reference and should be considered a part of this specification. This application is also related to the following U.S. Patent Applications: application Ser. No. 11/469,764 filed Sep. 1, 2006; application Ser. No. 11/165,652 filed Jun. 24, 2005; App. No. 60/713,521 filed Sep. 1, 2005; application Ser. No. 11/209,035 filed Aug. 22, 2005; App. No. 60/929,936 filed Apr. 30, 2007; App. No. 60/899,487 filed Feb. 5, 2007; and application Ser. No. 12/024,969 filed Feb. 1, 2008. The entire contents of all of the above applications are hereby incorporated by reference and should be considered a part of this specification.

BACKGROUND OF THE INVENTION

1. Field of the Invention

The present invention relates to bone cement injection systems and methods for osteoplasty procedures, such as vertebral compression fractures. In particular, one embodiment provides a system for controlling the viscosity of bone cement to a desired level prior to delivery into bone. Another embodiment provides a system for controlling the flow rate of injected bone cement.

2. Description of the Related Art

Osteoporotic fractures are prevalent in the elderly, with an annual estimate of 1.5 million fractures in the United States alone. These include 750,000 vertebral compression fractures (VCFs) and 250,000 hip fractures. The annual cost of osteoporotic fractures in the United States has been estimated at $13.8 billion. The prevalence of VCFs in women age 50 and older has been estimated at 26%. The prevalence increases with age, reaching 40% among 80-year-old women. Medical advances aimed at slowing or arresting bone loss from aging have not proved solutions to this problem. Further, the population affected will grow steadily as life expectancy increases.

Osteoporosis affects the entire skeleton but most commonly causes fractures in the spine and hip. Spinal or vertebral fractures also cause other serious side effects, with patients suffering from loss of height, deformity and persistent pain which can significantly impair mobility and quality of life. Fracture pain usually lasts 4 to 6 weeks, with intense pain at the fracture site. Chronic pain often occurs when one vertebral level is greatly collapsed or multiple levels are collapsed.

Postmenopausal women are predisposed to fractures, such as in the vertebrae, due to a decrease in bone mineral density that accompanies postmenopausal osteoporosis. Osteoporosis is a pathologic state that literally means "porous bones". Skeletal bones are made up of a thick cortical shell and a strong inner meshwork, or cancellous bone, made up of collagen, calcium salts and other minerals. Cancellous bone is similar to a honeycomb, with blood vessels and bone marrow in the spaces. Osteoporosis is a condition of decreased bone mass leading to fragile bones with an increased risk of fractures. In an osteoporosis bone, the sponge-like cancellous bone has pores or voids that increase in dimension making the bone very fragile. In young, healthy bone tissue, bone breakdown occurs continually as the result of osteoclast activity, but the breakdown is balanced by new bone formation by osteoblasts. In an elderly patient, bone resorption can surpass bone formation thus resulting in deterioration of bone density. Osteoporosis occurs largely without symptoms until a fracture occurs.

Vertebroplasty and kyphoplasty are recently developed techniques for treating vertebral compression fractures. Percutaneous vertebroplasty was first reported by a French group in 1987 for the treatment of painful hemangiomas. In the 1990's, percutaneous vertebroplasty was extended to include osteoporotic vertebral compression fractures, traumatic compression fractures, and painful vertebral metastasis. Vertebroplasty is the percutaneous injection of PMMA (polymethylmethacrylate) into a fractured vertebral body via a trocar and cannula. The targeted vertebrae are identified under fluoroscopy. A needle is introduced into the vertebrae body under fluoroscopic control, to allow direct visualization. A bilateral transpedicular (through the pedicle of the vertebrae) approach is typical but the procedure can be done unilaterally. The bilateral transpedicular approach allows for more uniform PMMA infill of the vertebra.

In a bilateral approach, approximately 1 to 4 ml of PMMA is used on each side of the vertebra. Since the PMMA needs to be is forced into the cancellous bone, the techniques require high pressures and fairly low viscosity cement. Since the cortical bone of the targeted vertebra may have a recent fracture, there is the potential of PMMA leakage. The PMMA cement contains radiopaque materials so that when injected under live fluoroscopy, cement localization and leakage can be observed. The visualization of PMMA injection and extravasation are critical to the technique—and the physician terminates PMMA injection when leakage is evident. The cement is injected using syringes to allow the physician manual control of injection pressure.

Kyphoplasty is a modification of percutaneous vertebroplasty. Kyphoplasty involves a preliminary step consisting of the percutaneous placement of an inflatable balloon tamp in the vertebral body. Inflation of the balloon creates a cavity in the bone prior to cement injection. The proponents of percutaneous kyphoplasty have suggested that high pressure balloon-tamp inflation can at least partially restore vertebral body height. In kyphoplasty, some physicians state that PMMA can be injected at a lower pressure into the collapsed vertebra since a cavity exists, when compared to conventional vertebroplasty.

The principal indications for any form of vertebroplasty are osteoporotic vertebral collapse with debilitating pain. Radiography and computed tomography must be performed in the days preceding treatment to determine the extent of vertebral collapse, the presence of epidural or foraminal stenosis caused by bone fragment retropulsion, the presence of cortical destruction or fracture and the visibility and degree of involvement of the pedicles.

Leakage of PMMA during vertebroplasty can result in very serious complications including compression of adjacent structures that necessitate emergency decompressive surgery. See Groen, R. et al., "Anatomical and Pathological Considerations in Percutaneous Vertebroplasty and Kyphoplasty: A Reappraisal of the Vertebral Venous System", Spine, V. 29, No. 13, pp 1465-1471 (2004). Leakage or extravasation of PMMA is a critical issue and can be divided into paravertebral leakage, venous infiltration, epidural leakage and intradiscal leakage. The exothermic reaction of PMMA carries potential catastrophic consequences if thermal damage were to extend to the dural sac, cord, and nerve roots. Surgical evacuation of leaked cement in the spinal canal has been reported. It has been found that leakage of PMMA is related to various clinical factors such as the vertebral compression pattern, and the extent of the cortical fracture, bone mineral density, the interval from injury to operation, the amount of PMMA injected and the location of the injector tip. In one recent study, close to 50% of vertebroplasty cases resulted in leakage of PMMA from the vertebral bodies. See Hyun-Woo Do et al., "The Analysis of Polymethylmethacrylate Leakage after Vertebroplasty for Vertebral Body Compression Fractures", J. Korean Neurosurg. Soc., V. 35, No. 5 (2004) pp. 478-82, (http://www.jkns.or.kr/htm/abstract.asp? no=0042004086).

Another recent study was directed to the incidence of new VCFs adjacent to the vertebral bodies that were initially treated. Vertebroplasty patients often return with new pain caused by a new vertebral body fracture. Leakage of cement into an adjacent disc space during vertebroplasty increases the risk of a new fracture of an adjacent vertebral body. See Am. J. Neuroradiol., 25(2):175-80 (February 2004). This study found that 58% of vertebral bodies adjacent to a disc with cement leakage fractured during the follow-up period, compared with 12% of vertebral bodies adjacent to a disc without cement leakage.

Another life-threatening complication of vertebroplasty is pulmonary embolism. See Bernhard, J. et al., "Asymptomatic diffuse pulmonary embolism caused by acrylic cement: an unusual complication of percutaneous vertebroplasty", Ann. Rheum. Dis., 62:85-86 (2003). The vapors from PMMA preparation and injection also are cause for concern. See Kirby, B. et al., "Acute bronchospasm due to exposure to polymethylmethacrylate vapors during percutaneous vertebroplasty", Am. J. Roentgenol., 180:543-544 (2003).

In both higher pressure cement injection (vertebroplasty) and balloon-tamped cementing procedures (kyphoplasty), the methods involved do not provide for well controlled augmentation of vertebral body height. The direct injection of bone cement simply follows the path of least resistance within the fractured bone. The expansion of a balloon also applies compacting forces along lines of least resistance in the collapsed cancellous bone. Thus, the reduction of a vertebral compression fracture is not optimized or controlled in high pressure balloons as forces of balloon expansion occur in multiple directions.

In a kyphoplasty procedure, the physician often uses very high pressures

Kyphoplasty also does not provide a distraction mechanism capable of 100% vertebral height restoration. Further, kyphoplasty balloons under very high pressure typically apply forces to vertebral endplates within a central region of the cortical bone that may be weak, rather than distributing forces over the endplate.

SUMMARY OF THE INVENTION

There is a general need to provide bone cement delivery systems and methods for use in treatment of vertebral compression fractures that provide a greater degree of control over introduction of cement.

In accordance with one embodiment an apparatus for bone cement delivery is provided. The apparatus can have a handle body defining a flow channel extending therethrough from an inlet of the body to an outlet of the body, the inlet of the handle body detachably coupleable to a source of bone cement, the outlet of the handle body detachably coupleable to an elongated bone cement injector and a thermal energy emitter disposed in the handle body in communication with the flow channel, the thermal energy emitter configured to apply energy to bone cement passing through the flow channel. In certain embodiments, the thermal energy emitter can be disposed about the flow channel such that bone cement flows through the emitter.

In some embodiments the thermal energy emitter can comprise a PTCR heater with spaced apart opposing polarity electrodes. In certain embodiments the handle body can further define a second channel co-linear with the elongated bone cement injector. The second channel can be configured to allow insertion of a tool therethrough into the bone cement injector.

In an additional embodiment a system for delivering a bone fill material into a bone is provided. The system can comprise a handle body, a thermal energy emitter, a source of bone fill material and an elongated injector. The handle body can define a flow channel and the thermal energy emitter can be disposed in the handle body in communication with the flow channel. The thermal energy emitter can apply energy to a bone fill material passing through the flow channel. The bone fill material can reside in the source of bone fill material which can be detachably coupled to the handle body. The elongated injector can be detachably coupleable to the handle body such that a bore through the injector is in communication with the flow channel, the injector configured to allow flow of bone fill material therethrough to an outlet opening at a distal portion of the injector into a bone.

Other embodiments of the system can further comprise an energy source coupleable to the thermal energy emitter. The energy source of certain embodiments can comprise at least one of a voltage source, a radiofrequency source, an electromagnetic energy source, a non-coherent light source, a laser source, an LED source, a microwave source, a magnetic source and an ultrasound source. Other embodiments of the system can further comprise a controller. The controller can be configured to control the polymerization rate of the bone fill material flowing through the flow channel to achieve a generally constant bone fill material viscosity at the outlet opening of the injector.

A further embodiment provides a method for treating a bone. The method can comprise inserting part of an elongated bone cement injector percutaneously through a patient's skin into a bone, coupling an injector to a handle body, coupling a source of bone cement to the handle body, flowing bone cement from the source of bone cement through the handle body and through a bore in the injector into the bone and applying energy to the bone cement as it flows through the handle body. Applying energy to the bone cement can accelerate the setting rate in the bone cement so as to reach a selected polymerization endpoint as the bone cement exits the injector. In some embodiments the selected polymerization endpoint provides a bone cement viscosity that substantially inhibits extravasation of bone cement upon introduction of the bone cement into the bone.

Certain embodiments of the method can further comprise the step of modulating the applied energy via a controller based at least in part on a signal indicative of a temperature of the bone cement that is communicated to the controller. Alternatively, or additionally, other embodiments can include the step of modulating the applied energy via a controller based at least in part on a signal indicative of a flow rate of the bone cement that is communicated to the controller.

Certain embodiments of the method can further comprise the step of introducing a tool into a bore of the injector while at least a portion of the cannula is positioned in the cancellous bone. This step, in certain embodiments, can be for extending the tool through the injector to obtain a biopsy tissue.

In accordance with another embodiment a system for delivering bone fill material into a bone is provided. The system can comprise an injector body, a bone fill material container, a low pressure drive mechanism and a high pressure drive mechanism. The injector body can comprise a handle portion and an elongated cannula attached to the handle portion. The bone fill material container can be removably coupleable to the injector body. The low pressure drive mechanism can be coupled to the bone fill material container. The low pressure drive mechanism can operate below about 10 psi and can effect a flow of bone fill material from the container to the injector body. The high pressure drive mechanism can also be operatively coupleable to the injector body. The high pressure drive mechanism can operate above about 20 psi and can effect a flow of bone fill material through the injector body and into the bone.

In certain embodiments the system can comprise a one-way valve positioned in the bone fill material container or in the injector body. In some embodiments the system can comprise a flow control mechanism configured to generate a bone fill material flow rate signal. In some embodiments the system can comprise a flow meter device.

In accordance with one embodiment a bone cement injection system for osteoplasty procedures is provided. The system can comprise a bone cement injector body, a bone cement container and a one-way valve. The bone cement injector body can have a handle portion and a distal end portion with a flow channel extending therethrough. The bone cement container can couple to the bone cement injector and it can have a flow passage in communication with the flow channel. The one-way valve can be positioned in the flow passage or in the flow channel.

A further embodiment provides a method for delivering bone cement into a vertebra. The method can comprise providing a bone cement injector system and applying pressure to flow bone cement. The bone cement injector system can comprise a low-pressure drive system configured to move cement from a bone cement container to a bone cement injector at a pressure of less than about 10 psi and a high pressure drive system configured to move bone cement through the bone cement injector and into a cancellous bone portion of a vertebra at a pressure of greater than about 20 psi. The step of applying pressure can comprise applying a pressure of less than about 10 psi to flow bone cement from the bone cement container to the injector. The step of applying pressure can further comprise applying a pressure of greater than about 20 psi to flow the bone cement through the injector and into the vertebra.

In certain embodiments the method can comprise applying a selected level of energy to the cement flow from a thermal energy emitter. In some embodiments the method can comprise providing bone cement flow rate signals to a controller.

According to an additional embodiment a system for delivering bone fill material into a bone is provided. The system can comprise an injector body, a flow control mechanism, a thermal energy emitter and a controller. The injector body can comprise a handle portion and an elongated cannula attached to the handle portion. The flow control mechanism can be disposed in the injector body and configured to generate a flow rate signal of bone fill material flowing through the injector body. The thermal energy emitter can be disposed in the injector body and configured to apply energy to the bone fill material flowing through the injector body. The controller can be configured to receive the flow rate signal from the flow control mechanism and to modulate at least one of the flow rate of bone fill material through the injector body and the energy applied by the thermal energy emitter to the bone fill material based at least in part on the flow rate signal.

In certain embodiments the flow rate signal can correspond to a measured electrical parameter of a PTCR or NTCR material that can respond to heat transfer from the bone fill material flow to the PTCR or NTCR material to thereby determine the flow rate of the bone fill material flow. In some embodiments this electrical parameter can be impedance.

An additional embodiment of the invention provides a method for injecting bone cement into a bone. The method can comprise inserting part of an injector body into a bone. The injector body can comprise a flow control mechanism configured to generate a flow rate signal of bone cement flowing through the injector body. The method can further comprise flowing bone cement through the injector body into the bone, generating a flow rate signal corresponding to the flow of bone cement through the injector body and modulating the application of thermal energy to the bone cement flowing through the injector body based at least in part on the flow rate signal.

According to another embodiment a method of delivering bone fill material into a bone is provided. The method can comprise inserting part of an injector body into a bone, the injector body comprising a PTCR or NTCR material, flowing a bone fill material through the injector body into the bone and measuring an electrical parameter of the PTCR or NTCR material in response to heat transfer from the flow of bone fill material to the PTCR or NTCR material to thereby determine a selected parameter of the bone fill material flow.

In some embodiments the measured electrical parameter can comprise an impedance value. In certain embodiments the selected parameter of the bone fill material can be any or all of: a flow rate, a temperature, and a viscosity. The method in certain embodiments can comprise modulating the flow rate of the bone fill material in response, at least in part, to determining the selected parameter.

In some embodiments the method can comprise applying energy to the bone fill material flow via a thermal energy emitter disposed in a handle portion of the injector body. The method can further comprise modulating at least one of the flow rate of the bone fill material flow and energy application to the bone fill material to maintain a substantially constant viscosity of the bone fill material flow ejected from the injector body over a desired injection interval.

These and other objects of the present invention will become readily apparent upon further review of the following drawings and specification.

BRIEF DESCRIPTION OF THE DRAWINGS

In order to better understand the invention and to see how it may be carried out in practice, some preferred embodiments are next described, by way of non-limiting examples only, with reference to the accompanying drawings, in which like reference characters denote corresponding features consistently throughout similar embodiments in the attached drawings.

DETAILED DESCRIPTION OF THE PREFERRED EMBODIMENTS

Figure 1:
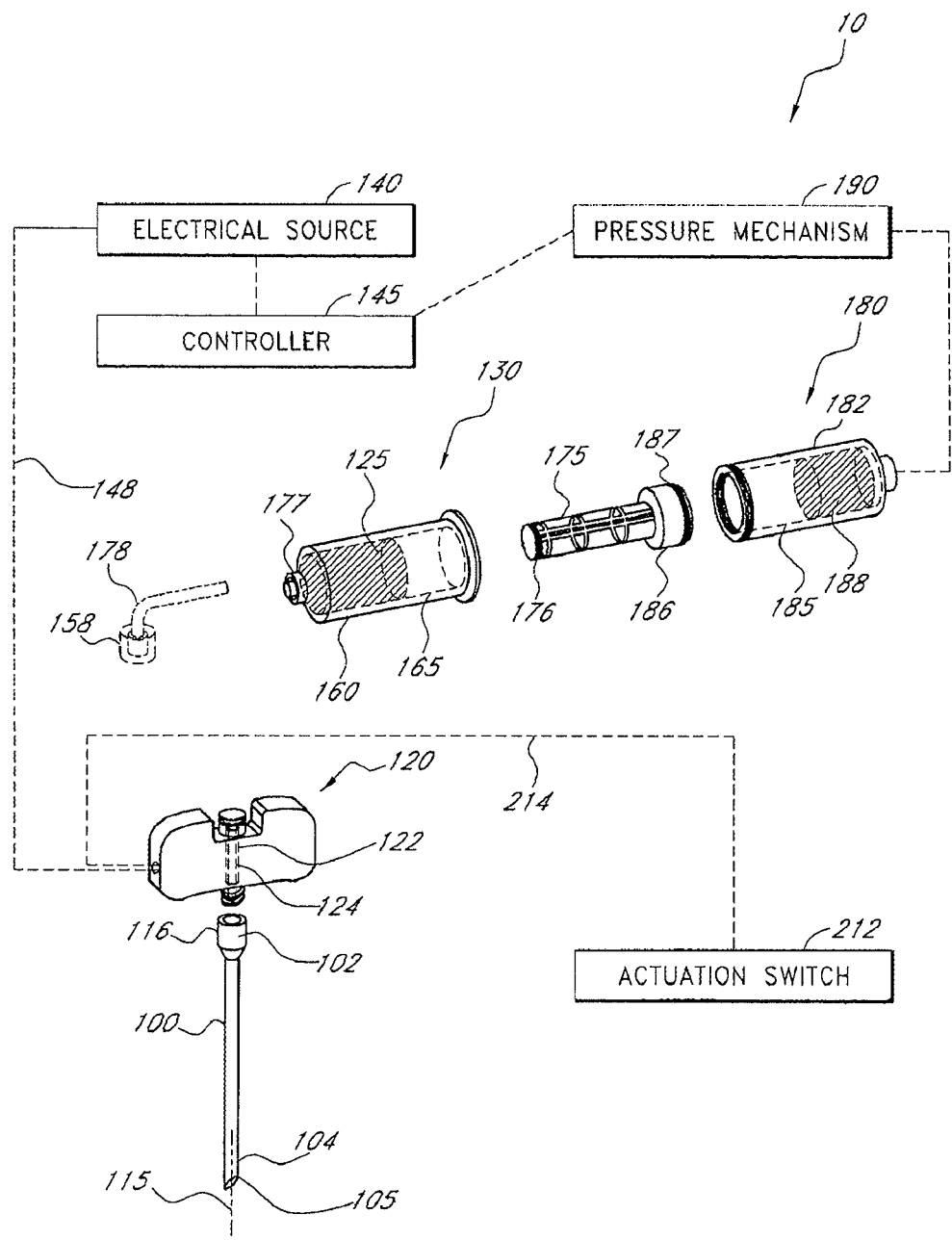
FIG. 1 is a schematic exploded view and block diagram of an embodiment of an injection system for delivering bone fill material into a bone.

For purposes of understanding the principles of the invention, reference will now be made to the embodiments illustrated in the drawings and the accompanying text. As background, a vertebroplasty procedure could include inserting an injector of the system of FIGS. 1-2 through a pedicle of a vertebra, or via a parapedicular approach, for accessing the osteoporotic cancellous bone. The initial aspects of the procedure can be similar to a conventional percutaneous vertebroplasty wherein the patient can be placed in a prone position on an operating table. The patient is typically under conscious sedation, although general anesthesia is an alternative. The physician can inject a local anesthetic (e.g., 1% Lidocaine) into the region overlying the targeted pedicle or pedicles as well as the periosteum of the pedicle(s). Thereafter, the physician can use a scalpel to make a 1 to 5 mm skin incision over each targeted pedicle. Thereafter, the introducer is advanced through the pedicle into the anterior region of the vertebral body, which typically is the region of greatest compression and fracture. The physician can confirm the introducer path posterior to the pedicle, through the pedicle and within the vertebral body by anteroposterior and lateral X-Ray projection fluoroscopic views. The introduction of infill material as described below can be imaged several times, or continuously, during the treatment depending on the imaging method.

Definitions

"Bone cement, bone fill or fill material, infill material or composition" includes its ordinary meaning and is defined as any material for infilling a bone that includes an in-situ hardenable material or that can be infused with a hardenable material. The fill material also can include other "fillers" such as filaments, microspheres, powders, granular elements, flakes, chips, tubules and the like, autograft or allograft materials, as well as other chemicals, pharmacological agents or other bioactive agents.

"Flowable material" includes its ordinary meaning and is defined as a material continuum that is unable to withstand a static shear stress and responds with an irrecoverable flow (a fluid)—unlike an elastic material or elastomer that responds to shear stress with a recoverable deformation. Flowable material includes fill material or composites that include a fluid (first) component and an elastic or inelastic material (second) component that responds to stress with a flow, no matter the proportions of the first and second component, and wherein the above shear test does not apply to the second component alone.

"Substantially" or "substantial" mean largely but not entirely. For example, substantially may mean about 50% to about 99.999%, about 80% to about 99.999% or about 90% to about 99.999%.

"Vertebroplasty" includes its ordinary meaning and means any procedure wherein fill material is delivered into the interior of a vertebra.

"Osteoplasty" includes its ordinary meaning and means any procedure wherein fill material is delivered into the interior of a bone.

Figure 2:
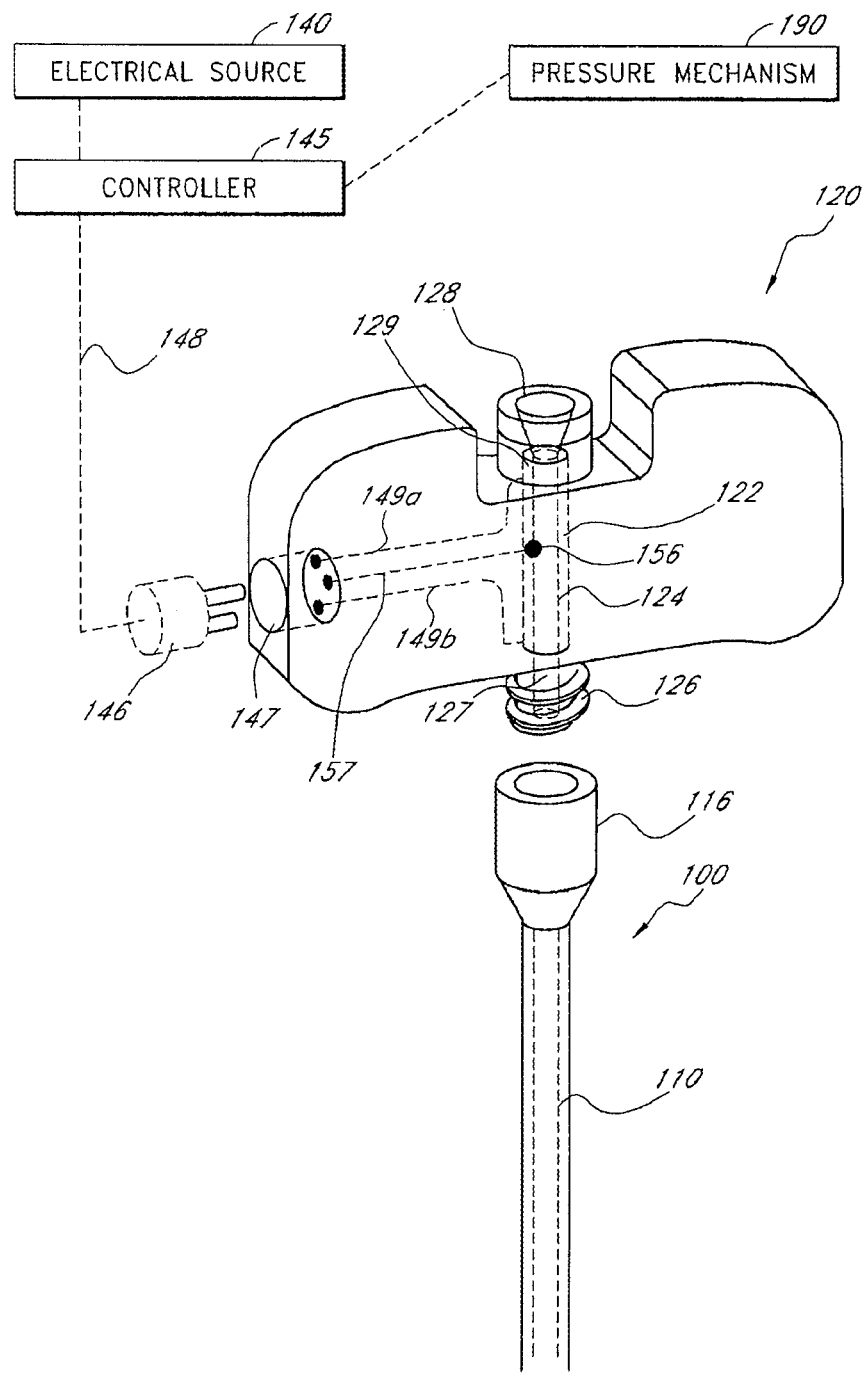
FIG. 2 is a schematic enlarged view of an energy-delivery component of the injection system of FIG. 1.

Now turning to FIGS. 1 and 2, a bone cement delivery system 10 is shown that includes a first component or bone cement injector 100 that can extend at least partially into a vertebra, which can be made of any suitable metal or plastic needle-like member with a proximal end 102 and a distal end 104 having flow outlet 105. The elongated injector 100 has a flow channel or bore 110 extending therethrough about axis 115 to the distal flow outlet 105. As can be seen in FIG. 1, the proximal end 102 of injector 100 has a fitting 116, such as a Luer fitting, for coupling a second cement delivery component 120 thereto, described below.

FIGS. 1 and 2 depict second component or handle body 120 that can be detachable and coupleable to fitting 116 and flow channel 110 in the injector 100. The second component 120 can include a thermal energy emitter 122 disposed about or proximate to flow channel 124 within the second component 120 for applying energy to bone cement 125 therein. Handle body 120 according to some embodiments can be an insulated body. Applying energy to the bone cement 125 can cause the cement to exhibit a different setting rate to reach a selected polymerization endpoint when the cement is introduced into the vertebra, as will be described in more detail below. FIG. 2 shows a fitting 126 of the second component 120 that can couple to fitting 116 of the first component 100, wherein a distal end 127 of flow channel 124 can thus communicate with flow channel 110 in the injector 100. Similarly, FIG. 2 shows a fitting 128 of the second component 120 that can couple a proximal end 129 of flow channel 124 with a bone cement source or third component 130, further described below.

In one embodiment, the energy emitter 122, can be integrated into the handle body 120. In some embodiments the energy emitter 122 can be glued in place within the handle body 120. In some embodiments the handle body 120 can be made from two handle halves and the energy emitter 122 can be captured within the in a recess when the two handle halves are put together.

Figure 3:
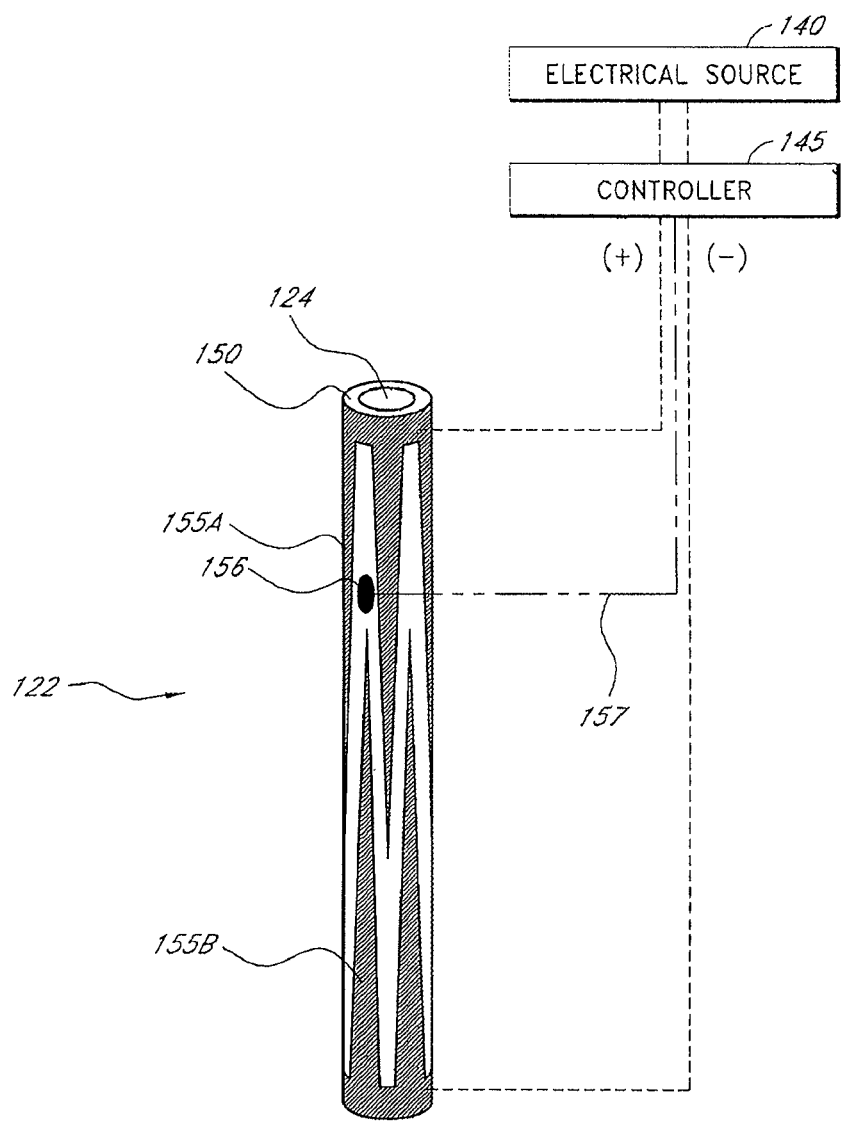
FIG. 3 is a schematic perspective view of one embodiment of a thermal emitter.

Referring to FIGS. 2 and 3, in one embodiment, the thermal energy emitter 122 can be coupled (e.g., electrically connected) to an electrical source 140 and a controller 145 by an electrical connector 146 and cable 148. In FIG. 2, it can be seen that electrical leads 149a and 149b can couple with connector 146 via a corresponding connector 147 and extend to the thermal energy emitter 122. As can be seen in FIG. 3, one embodiment of the thermal energy emitter 122 can have a wall portion 150 that can comprise a polymeric positive temperature coefficient of resistance (PTCR) material with spaced apart interlaced surface electrodes 155A and 155B, which are connected to the electrical leads 149a, 149b, respectively. Similarly the energy emitter 122 can be as that described in Provisional Application No. 60/907,468 filed Apr. 3, 2007 titled Bone Treatment Systems and Methods, and incorporated by reference above. In the illustrated embodiment, the thermal emitter 122 and wall 150 thereof can conduct heat to the bone cement 125 contained therein or passing therethrough to thereby cause controlled thermal effects in the bone cement 125. It should be appreciated that FIG. 3 is a schematic representation of one embodiment of thermal energy emitter 122 which can have any elongated or truncated shape or geometry, tapered or non-tapered form, or comprise the wall of a collapsible thin-wall element. Further, the positive (+) and negative (−) polarity electrodes 155A and 155B can have any spaced apart arrangement, for example radially spaced apart, helically spaced apart, axially spaced apart or any combination thereof The resistively heated PTCR material of the emitter 122 can, in one embodiment, farther generate a signal indicative of flow rate, as described in U.S. Provisional Application No. 60/907,468, which in turn can be communicated to and utilized by the controller 145 to modulate energy applied to the bone cement 125 therein, and/or modulate the flow rate of cement 125 which can be driven by a motor or a stored energy mechanism. In one embodiment illustrated in FIGS. 2 and 3, the emitter 122 can have a temperature sensor or thermocouple 156 fitted thereto with an electrical lead 157 coupling the sensor or thermocouple 156 to the controller 145 through connectors 146, 147 and cable 148. The thermocouple 156 can be position on the exterior of the emitter or within the flow channel 124 and can provide temperature feedback for allowing the controller to modulate an operating parameter.

In some embodiments, the lead lines 149a and 149b can be soldered onto electrodes 155A and 155B that can be painted onto the emitter 122. In one embodiment the emitter 122 is removable and it can be electrically connected to the lead lines 149a and 149b via electrical contacts that contact the electrodes 155A and 155B on the emitter 122.

Heat emitter 122 can comprise a conductive plastic. In some embodiment, heat emitter 122 can comprise a polymer PTCR material that can range from about 1 mm to 50 mm in length with any suitable bore 124 extending therethrough. In one embodiment, as in FIG. 3, the heat emitter 122 can be elongated with first and second opposing polarity electrodes 155A and 155B coupled to an electrical source 140 that can be an Rf source and controller 145 as described in previous embodiments. The PTCR material is known in the art and can comprise a polymeric material with dispersed conductive particles therein, which can be acquired from Bourns, Inc., 1200 Columbia Avenue, Riverside, Calif. USA 92507. In the illustrated embodiment of FIG. 3 which depicts the heat emitter 122 de-mated from the injector, it can be seen that the opposing polarity electrodes 155A and 155B are spaced apart and interdigitated to create uniform heating of the PTCR element to create a uniform heating of cement flows therethrough, with the electrodes 155A and 155B in one embodiment painted onto the PTCR material as a conductive ink or paint as is known in the art.

In other embodiments, the thermal energy emitter 122 can be a PTCR constant temperature heater as described above or selected from the group of emitters consisting of at least one of a resistive heater, a fiber optic emitter, a light channel, an ultrasound transducer, an electrode and an antenna. Accordingly in any such embodiment, the energy source 140 can comprise at least one of a voltage source, a radiofrequency source, an electromagnetic energy source, a non-coherent light source, a laser source, an LED source, a microwave source, a magnetic source and an ultrasound source, that is operatively coupled to the emitter 122.

Figure 4:
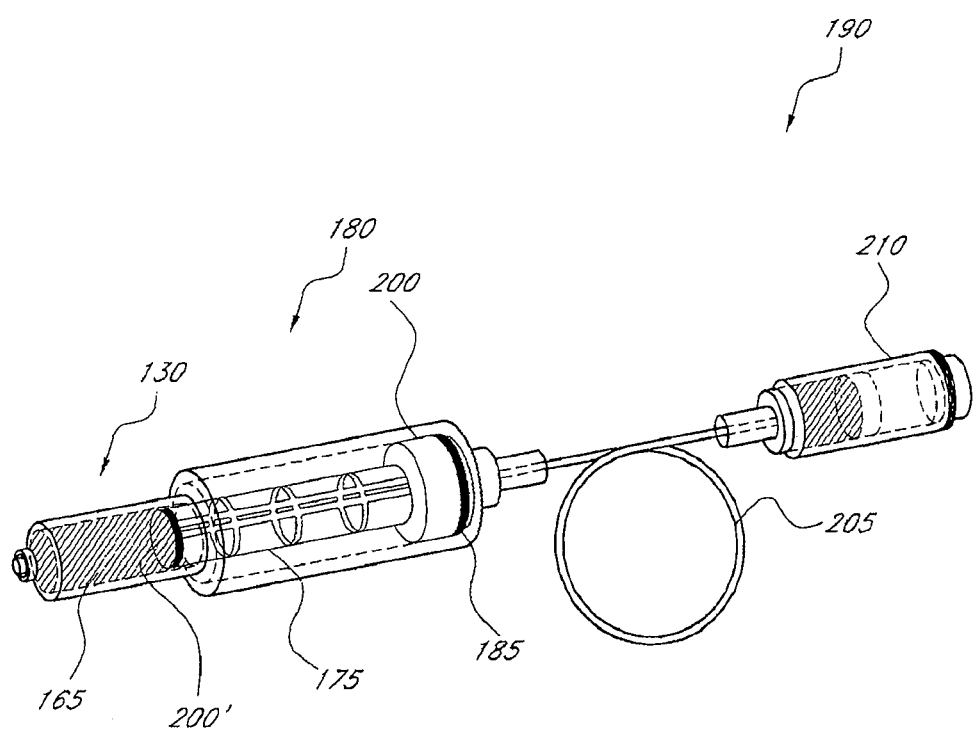
FIG. 4 is an enlarged transparent schematic view of components of the system of FIG. 1.

Referring now to FIGS. 1 and 4, in one embodiment, the bone cement source or third component 130 is shown with a fitting 158 that can detachably couple to the fitting 128 of the second energy delivery component 120. In the embodiment of FIGS. 1 and 4, the bone cement source 130 is shown with a syringe body 160 with cement-carrying bore or chamber 165 that can carry, in one embodiment, a pre-polymerized, partially polymerized or recently-mixed bone cement 125 therein. The assembly is further shown with a rigid plunger or actuator member 175 with o-ring or rubber head 176 that can slidably move in the chamber 165 to push the cement 125 through the syringe chamber 165 and the flow channels 110, 124 in the first and second components 100 and 120, respectively. In one embodiment, shown in the exploded view of FIG. 1, the outflow end portion 177 of the syringe can include an elbow 178 which can be rigid, deformable or flexible for convenient coupling to the second component 120.

Figure 5:
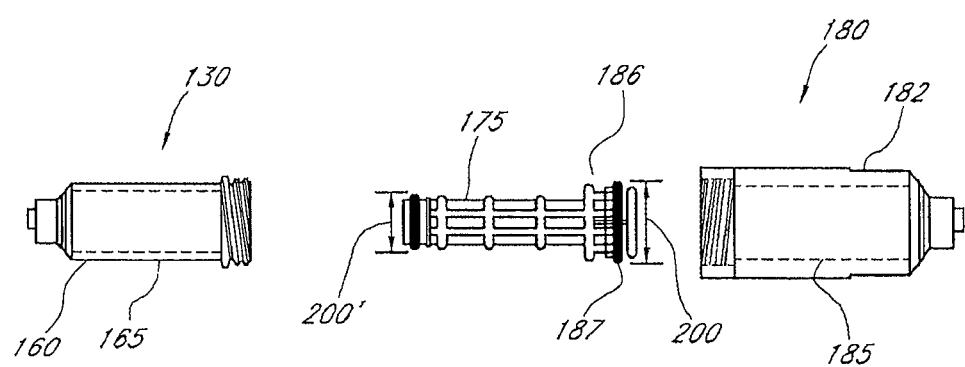
FIG. 5 is an exploded schematic view of components of FIG. 4.

FIGS. 1, 4 and 5, show one embodiment of a force application and amplification component 180 configured for de-matable coupling to bone cement source 130 and more particularly to syringe 160. The component 180 can comprise a body 182 with a pressurizable bore or chamber 185 therein that can slidably receive a proximal end 186 of the actuator member 175. The proximal end 186 of the actuator member 175 can include an o-ring or gasket 187 so that bore 185 can be pressurized with flow media 188 by pressure source 190 to drive actuator member 175 distally to thereby displace bone cement 125 from chamber 165 in the syringe body 160. In one embodiment, the surface area of an interface 200 between the actuator member 175 and the pressurized flow media 188 can be substantially larger than the surface area of interface 200' between the actuator member 175 and the bone cement 125. The difference in surface area between the two interfaces 200, 200' can provide pressure amplification between the pressurizable chamber 185 and the syringe chamber 165. In one embodiment as indicated in FIGS. 4 and 5, the surface area of interface 200 can be at least 150% of the surface area of interface 200', at least 200% of the surface area of interface 200', at least 250% of the surface area of interface 200' and/or at least 300% of the surface area of interface 200'.

Referring to FIGS. 4 and 5, in one embodiment, a force amplification method of the invention can include (a) providing a bone fill material injector with a displaceable non-fluid actuator component intermediate a first fluid chamber and a second cement or fill-carrying chamber; (b) causing a flow of flow media at a first pressure into the first fluid chamber thereby displacing the actuator component to impinge on and eject bone cement or fill at a higher second pressure from the second chamber into a vertebra. The method can provide a second pressure in the cement-carrying chamber 165 that is: at least 50% higher that the first pressure in the pressurizable chamber 185, at least 50% higher than the first pressure in the pressurizable chamber 185, at least 100% higher than the first pressure in the pressurizable chamber 185, at least 200% higher than the first pressure in the pressurizable chamber 185, at least 300% higher that the first pressure in the pressurizable chamber 185.

Figure 6:
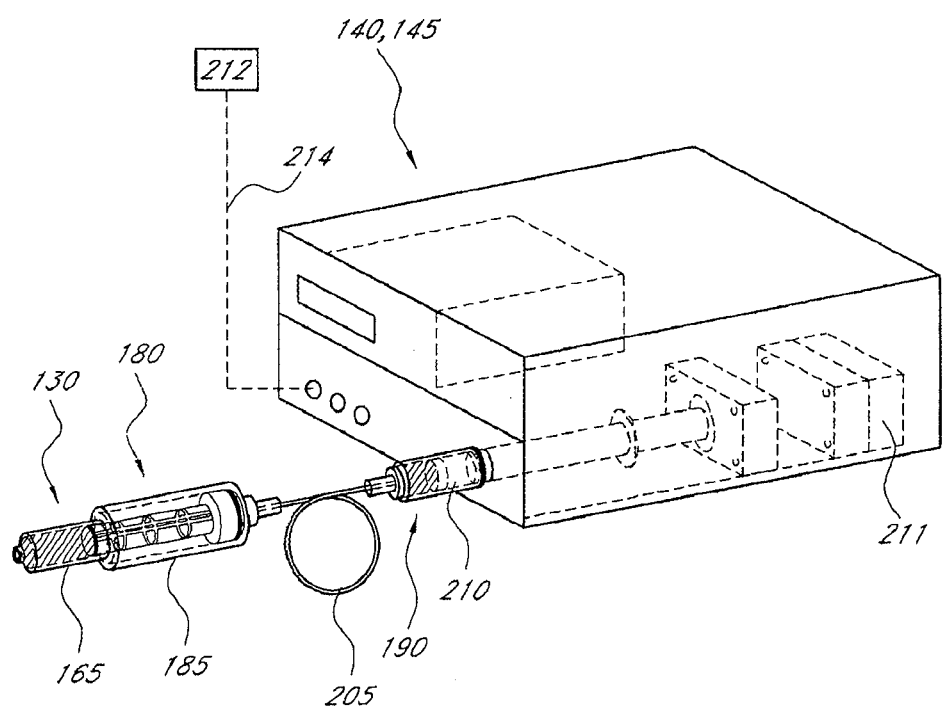
FIG. 6 is a perspective schematic view of components of the system of FIGS. 1 and 4 with the energy source and controller.

Referring to FIGS. 4 and 6, one embodiment of a pressurizing mechanism can include a pneumatic or hydraulic line 205 that extends to pressure source 190. The pressure source 190 can, in one embodiment, include a syringe pump 210 that can be manually driven or motor-driven. In the embodiment of FIG. 6, the syringe pump 210 is shown driven by an electric motor 211 operatively coupled to controller 145 to allow modulation of pressure or driving force in combination with control of energy delivery to the emitter 122 from energy source 140. It should be appreciated that the pressurizing mechanism or pressure source 210 can be any suitable type of mechanism or pump that can actuate the actuator member 175 to move the bone cement in the chamber 165. For example, a suitable mechanism can be a piezoelectric element for pumping fluid, an ultrasonic pump element, a compressed air system for creating pressure, a compressed gas cartridge for creating pressure, an electromagnetic pump for creating pressure, an air-hammer system for creating pressure, a mechanism for capturing forces from a phase change in a fluid media, a spring mechanism configured for releaseably storing energy, a spring mechanism and a ratchet, a fluid flow system and a valve, a screw pump, a peristaltic pump, a diaphragm pump, a rotodynamic pump or a positive displacement pump.

Returning back to FIG. 1, the system 10 can, in one embodiment, include a remote switch 212 for actuating at least the pressure mechanism 180. In some embodiments a cable 214 can extend from either the first component 100, second component 120 or third component 130 so that the physician can stand outside of the radiation field created by any imaging system used while operating the system 10 to, for example, treat a vertebra. In another embodiment, the switch 212 can be wirelessly connected to the system 10. In another embodiment as shown in FIG. 6, the elongated cable 214 and switch 212 can be directly coupled to the energy source 140 and/or the controller 145.

Figure 7:
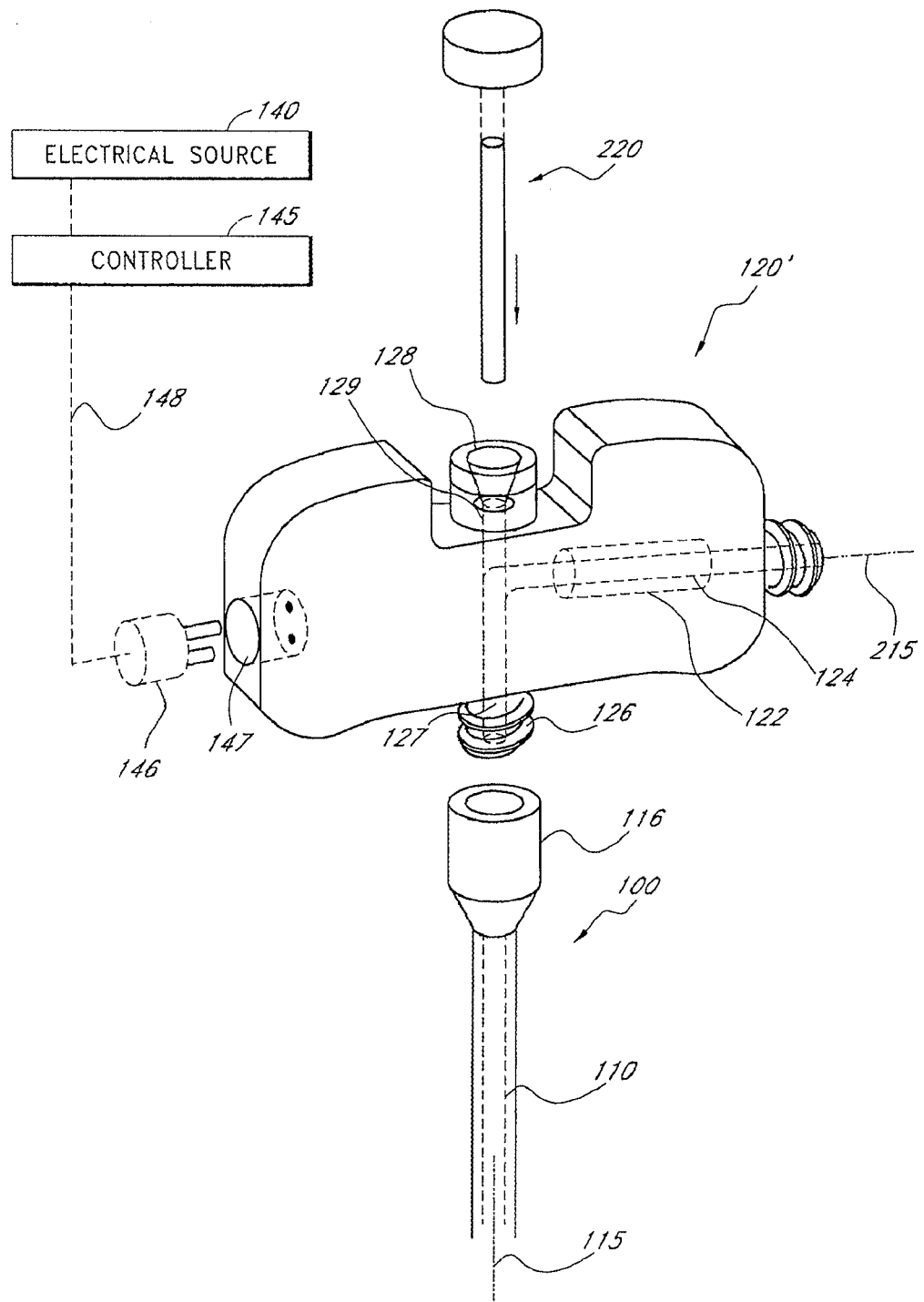
FIG. 7 is another embodiment of an energy-delivery component of an injection system for delivering bone fill material into a bone.

Now referring to FIG. 7, another embodiment of the energy delivery component or second component 120' shows the emitter 122 and flow channel 124 therein extending about a second axis 215 that is not aligned with the first axis 115 of the injector 100. This arrangement can allow for a tool 220 to be introduced axially, along the first axis 115, through the injector channel 110 without de-coupling the second energy delivery component 120' from the injector 100. Some example embodiments of the tool 220 follow. The tool 220 can be used to clear the flow channel 110 in injector 100. Tool 220 can clear the outlet 105 (FIG. 1). The tool 220 can be flexible or rigid. The tool 220 can be introduced into bone to perform a procedure such as cutting bone, obtaining a biopsy sample, creating a pathway, expanding a pathway with an expandable member and the like.

Figure 8:
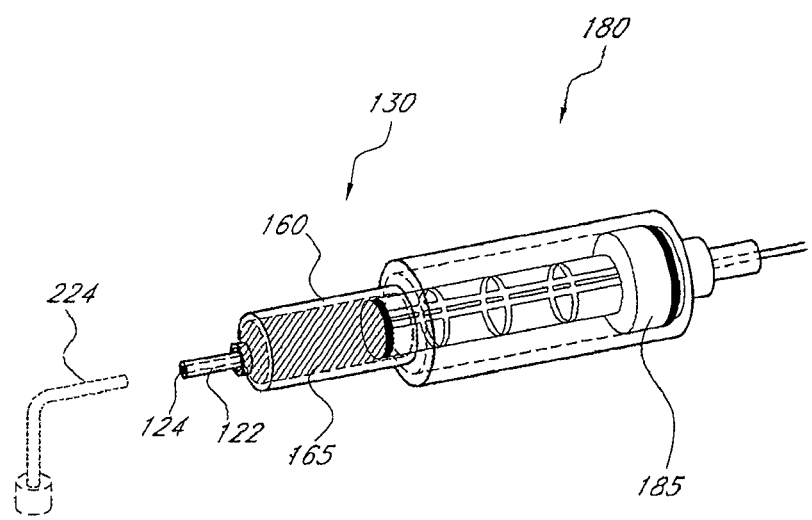
FIG. 8 is a partial schematic view of another embodiment of an injection system for delivering bone fill material into a bone.

FIG. 8 depicts another embodiment of a bone treatment system that combines the energy-delivery or second component 120 of FIGS. 1-2 with the bone cement source 130 of FIGS. 2 and 4. As can be seen in the embodiment illustrated in FIG. 8, the thermal energy emitter 122 and flow channel 124 therein can be a component of the syringe 160 and chamber 165 therein. In one embodiment, the energy emitter 122 can be detachably coupled to the syringe 160. In another embodiment, the energy emitter 122 can be integrated into and unitary with the syringe 160. The emitter 122 can be connected to energy source 140 as described previously, and can extend with a unitary or de-coupleable member indicated at 224 that can be coupled to the second component 120. The de-coupleable member 224 can be straight or curved and can be rigid, flexible or deformable to connect to a cement injection cannula. In some embodiments, the thermal energy emitter 122 can be integrated into any of: the syringe chamber or cement-carrying member, the outflow channel exiting the syringe, a rigid or flexible conduit coupling the syringe to the cement injection needle, a handle or proximal end of the cement injection needle, the distal end of the cement injection needle, a sleeve configured for introduction into any of the above components, or a sleeve-like component configured for positioning about an exterior of any of the above components. It should be appreciated that certain embodiments of the system can further include first and second emitters or any plurality of emitters within different portions of the system.

Figure 9:
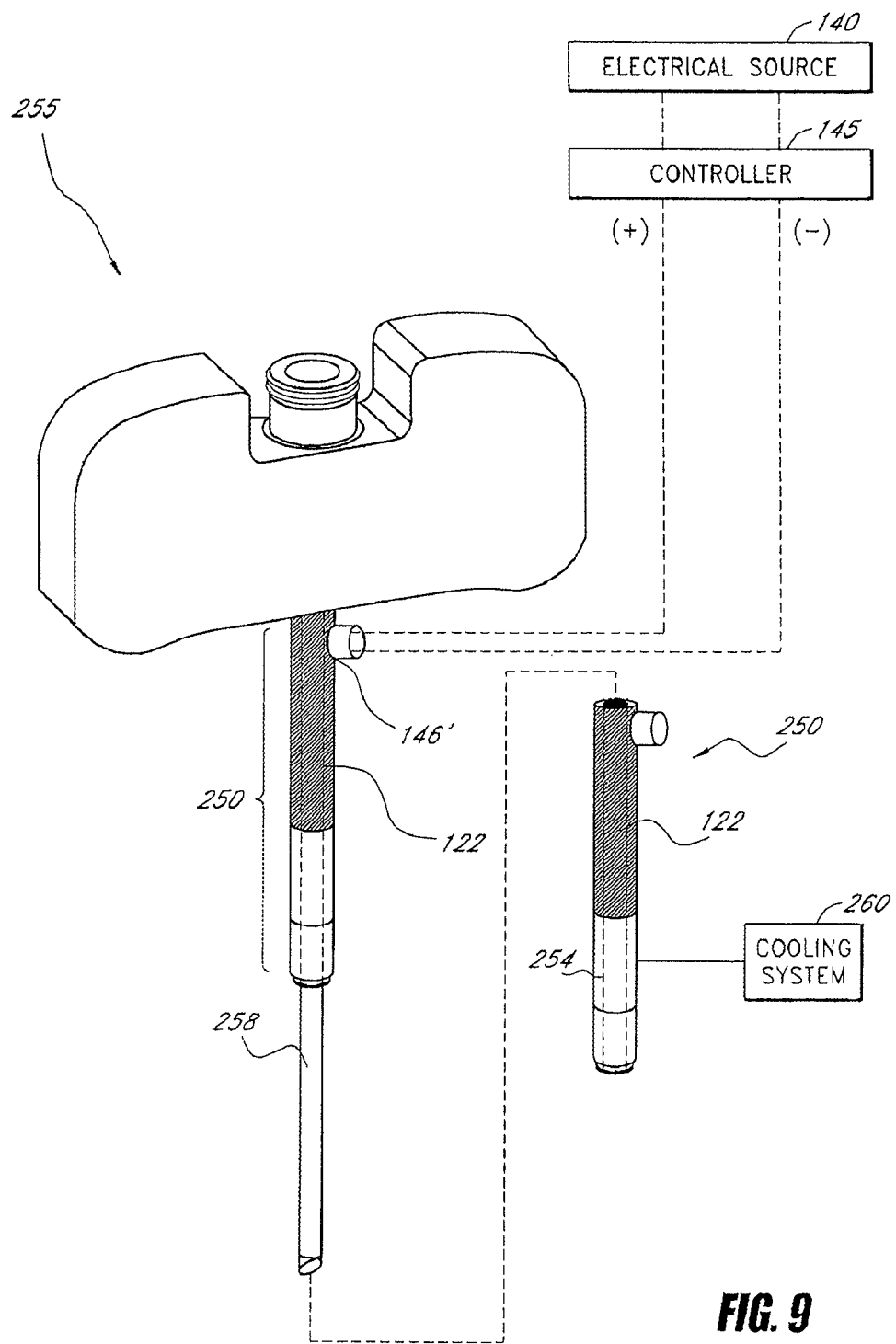
FIG. 9 is a schematic view of another embodiment of an injection system for delivering bone fill material into a bone.

FIG. 9 depicts another embodiment of a bone cement injector system that can include an energy-delivery component 250 with a heating element 122 therein similar to that of FIGS. 2-3 (e.g., a PTCR heating element). In this embodiment, the energy-delivery component 250 can be a separate component that can be used to retrofit a commercially available injector system 255. The energy-delivery component 250 can have a bore 254 that can receive cannula 258 with a sliding fit to allow heat from PTCR heating element 122 to conduct heat through the wall of the cannula 250 to bone cement in the cannula 258. In some embodiments the sliding fit can be a press-fit connection. The energy source 140 and controller 145 can be operatively coupled to the PTCR heating element 122 via connector 146' as described previously. The surface of the second component 250 can be coated with an insulative material. In FIG. 9, the second component 250 is illustrated for convenience as a sleeve but it should be appreciated that the component can be rigid, flexible, clampable, a flexible wrapping member, singular or plural and the component may be coupled to any portion of the system including the cannula, syringe, or cement-carrying conduit.

Still referring to FIG. 9, another embodiment can include a cooling system 260 such as a circulating fluid or Peltier element for cooling the cement and for protecting the skin from contact with a cannula that may be at an elevated temperature.

In one embodiment of the system, the bone cement 125 can have a predetermined working time for polymerizing from an initial state to a selected endpoint of at least 10 minutes, 12 minutes, 14 minutes, 16 minutes, 18 minutes, 20 minutes, 25 minutes, 30 minutes and/or 40 minutes, as disclosed in Provisional application Ser. No. 60/899,487 filed Feb. 5, 2007 titled Bone Treatment Systems and Methods, and U.S. application Ser. No. 12/024,969, filed Feb. 1, 2008. The selected endpoint is defined as providing the bone cement 125 in a partly polymerized condition having a selected viscosity range that substantially prevents cement extravasation. Herein, the terms 'polymerization rate', 'working time' and 'setting time' may be used alternatively to describe the interval in which the cement polymerizes from the initial or just-mixed state to the selected endpoint. Setting time is measured in accordance with ASTM standard F451, "Standard Specification for Acrylic Bone Cement," which is hereby incorporated by reference in its entirety. Viscosity is also measured according to ASTM standard F451.

As can be understood from FIG. 2, the energy source 140 can be configured for accelerating a polymerization rate of the bone cement by at least 20%, 30%, 40%, 50%, 60%, 70%, 80%, 90% and/or 95%. In other embodiments, the energy source 140 and controller 145 can be configured for accelerating the polymerization rate of the cement to the selected endpoint in less than 1 second, 5 seconds, 10 seconds, 20 seconds, 30 seconds, 45 seconds, 60 seconds and/or 2 minutes.

A method of using the system 10 of FIGS. 1-6 to treat a vertebra can comprise (i) introducing at least a portion of the cement injector needle 100 into a vertebra, the needle 100 having a flow channel 110 extending from a proximal injector end 102 to a distal injector end 104 with a flow outlet 105; (ii) causing a flow of bone cement 125 from the source 130 through a flow channel in the an energy-delivery component 120 and the injector needle 100; and (iii) applying energy from the energy-delivery component 120 to the flow to cause the cement 125 to exhibit a different setting rate to reach a selected polymerization endpoint. In this method, the applied energy can further accelerate setting of pre-polymerized bone cement 125 before exiting the flow outlet 105. The method and the selected polymerization endpoint can provide a viscosity that can substantially prevent cement extravasation following introduction into the vertebra (e.g., following delivery of the bone cement 125 into cancellous bone within the vertebral body).

In some embodiments of the method, the energy-delivery component 120 can be detachably coupled to the bone cement source 130 and to the proximal end 102 of the injector needle 100.

In another embodiment of the method, the energy-delivery component 120 can be actuated by the operator from a location outside any imaging field.

In another embodiment of the method, the energy-delivery component 120 can be actuated to apply energy of at least 0.01 Watt, 0.05 Watt, 0.10 Watt, 0.50 Watt and/or 1.0 Watt. In another aspect of the method, the applied energy can be modulated by controller 145 to maintain a selected temperature as measured by temperature sensor 156 (FIGS. 2-3) or to provide a selected temperature profile over time as cement flows through the emitter 122. In other embodiments of the method, the energy source 140 and controller 145 can be configured for accelerating the polymerization rate of the bone cement to the selected endpoint in less than 1 second, 5 seconds, 10 seconds, 20 seconds, 30 seconds, 45 seconds, 60 seconds and/or 2 minutes. In other embodiments of the method, the energy source 140 and controller 145 can be configured for accelerating the polymerization rate by at least 20%, 30%, 40%, 50%, 60%, 70%, 80%, 90% and/or 95%.

Figure 10:
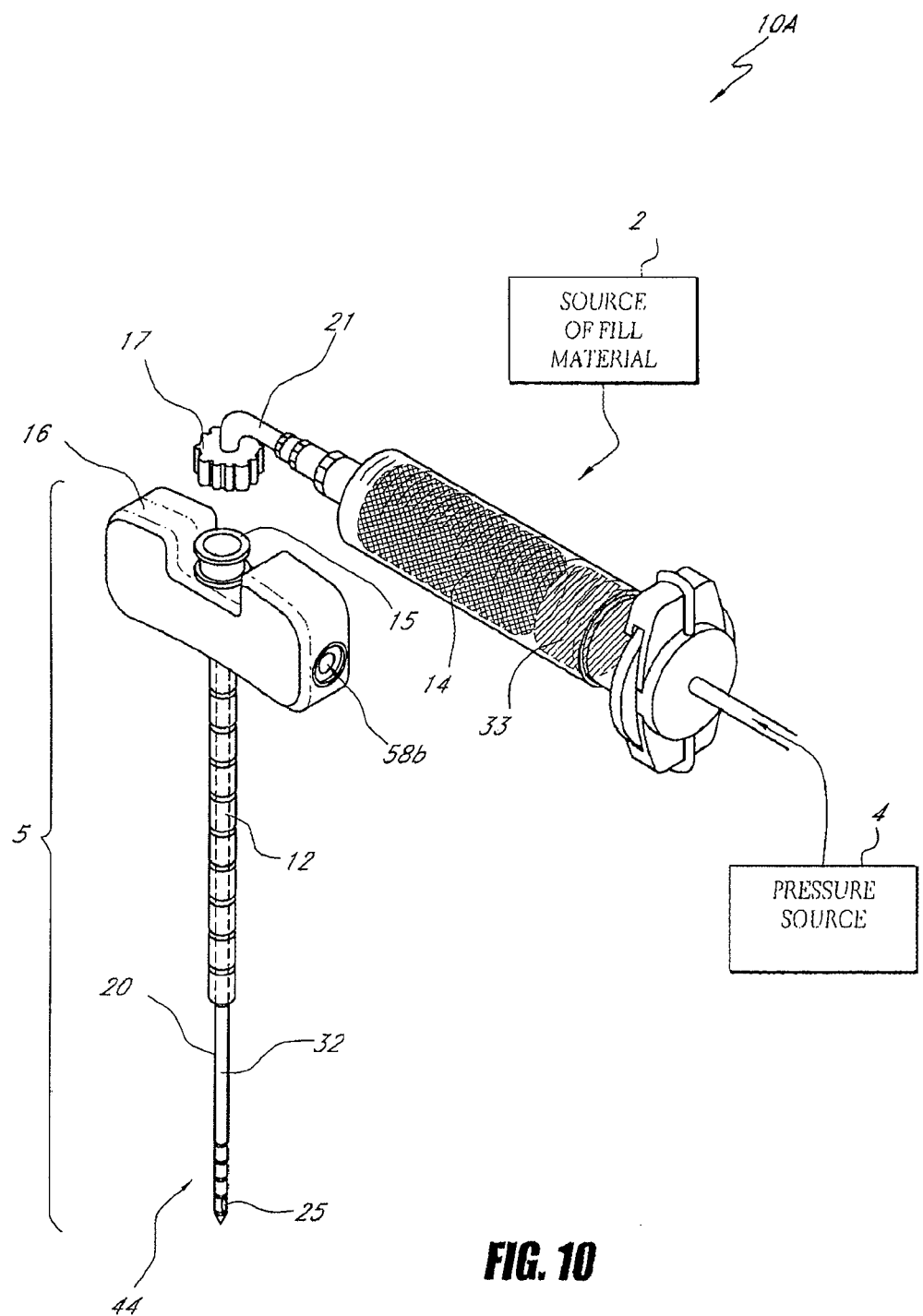
FIG. 10 is a schematic perspective view of another embodiment of an injection system for delivering bone fill material into a bone.
Figure 11:
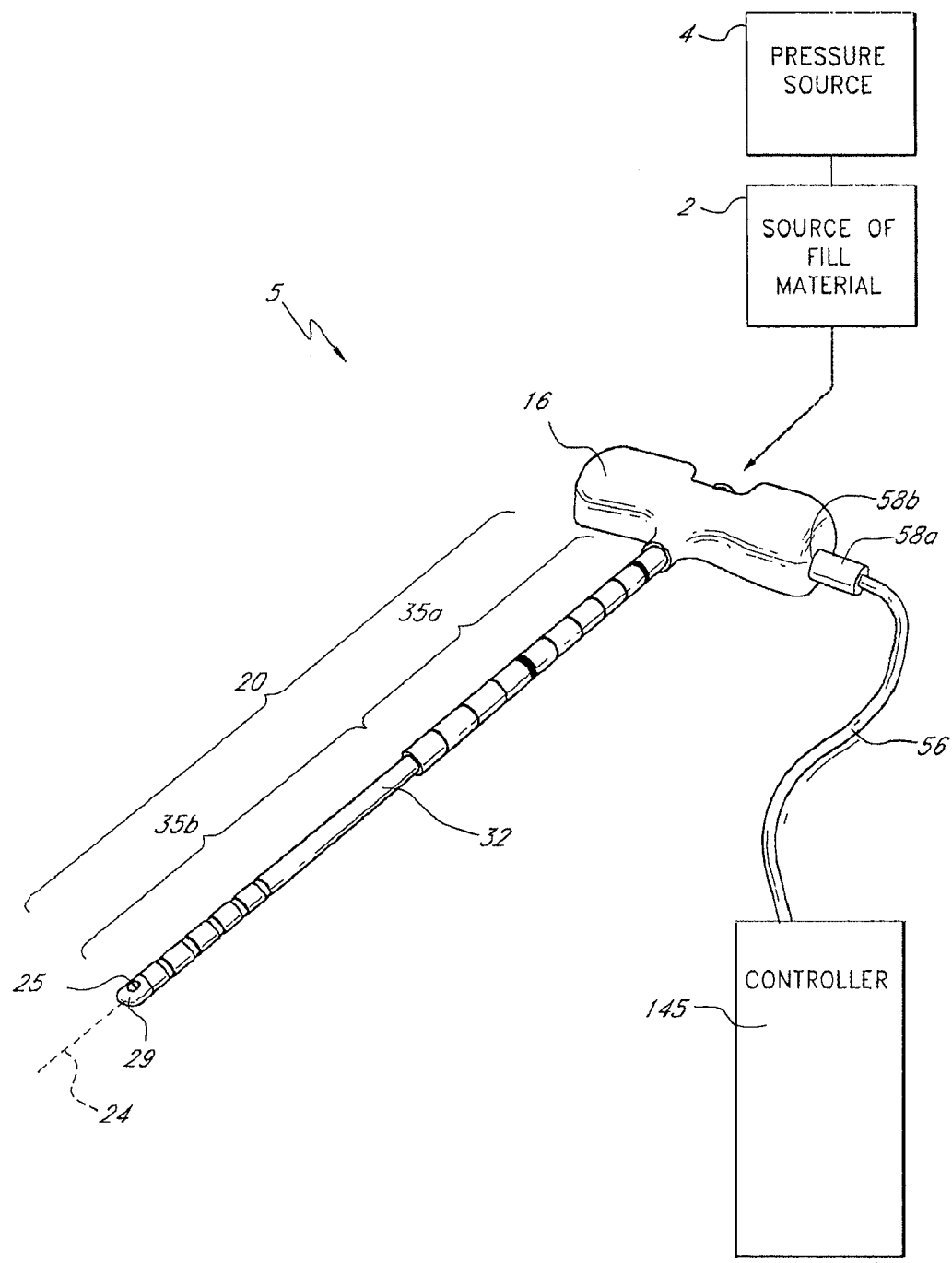
FIG. 11 is another schematic perspective view of the bone cement injector of FIG. 10.

Referring now to FIGS. 10-11, another embodiment of a bone fill introducer or injector system 10A is shown configured for treatment of the spine in a vertebroplasty procedure. The system 10A can include a bone cement injector 5 coupled to source 2 of a bone fill material wherein the injection of the fill material can be carried out by a pressure mechanism or source 4 operatively coupled to source 2 of the bone fill material. In one embodiment as in FIG. 1, the pressure source 4 can be a computer controlled hydraulic actuator, but the scope of the invention includes a manually operated syringe loaded with bone fill material, or any other pressurized source of fill material. The source 2 of fill material can include a coupling or fitting 17 for sealable locking to a cooperating fitting 15 at a proximal end or handle 16 of the bone cement injector 5 that can have an elongated introducer sleeve 20. In one embodiment, a syringe-type source 2 can be coupled directly to fitting 15 with a flexible, rigid or bendable (deformable) hydraulic tube 21 extending to pressure source 4. The fill material then can flow through handle 16 to communicate with a passageway 12 in introducer sleeve 20.

Figure 12:
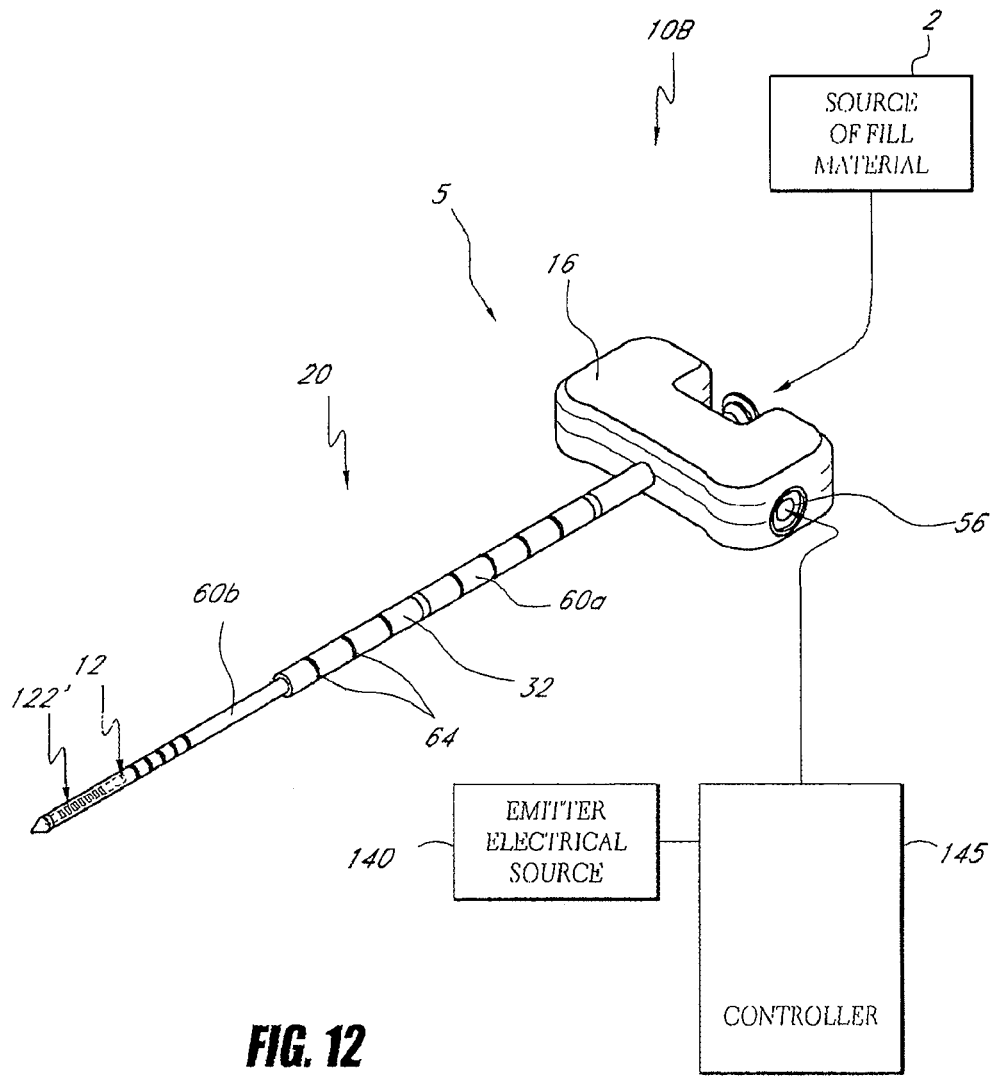
FIG. 12 is a schematic cut-away view of another embodiment of a bone cement injector similar to that of FIGS. 10-11.
Figure 13:
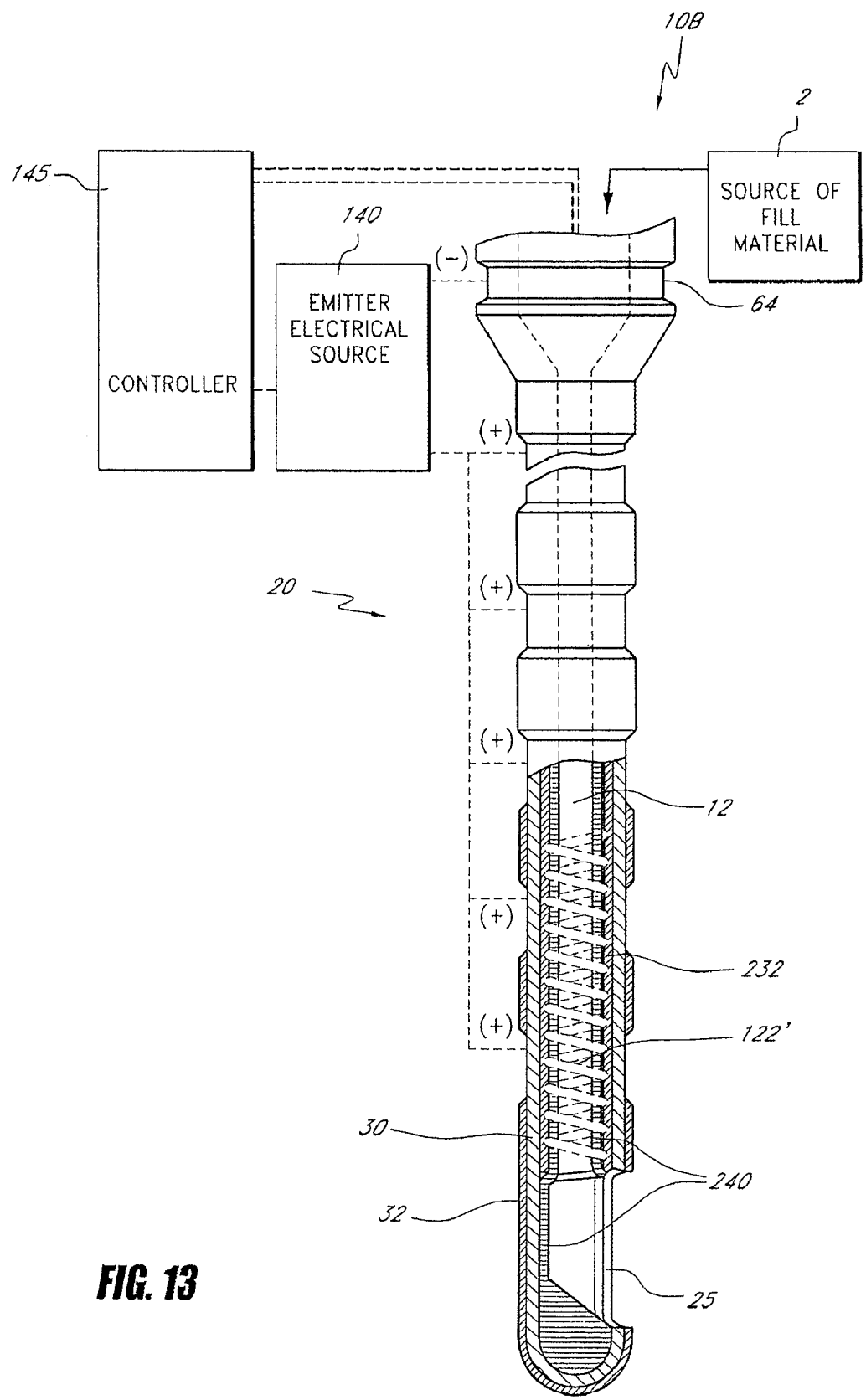
FIG. 13 is a schematic sectional view of a distal portion of the bone cement injector of FIGS. 10-11 with a thermal energy emitter in an interior bore of the injector and a scratch-resistant insulative exterior coating.

In FIGS. 10-13, it can be seen that elongated introducer sleeve 20 of bone cement injector 5 has an interior channel 12 extending about axis 24 and terminating in a distal open outlet 25. The outlet 25 can be a single opening or a plurality of openings about the radially outward surface of sleeve 20 or an opening at a distal tip 29 the sleeve. The distal tip 29 can be blunt or sharp. In one embodiment as illustrated in FIG. 13, a core portion 30 of sleeve 20 can be an electrically conductive metal sleeve, such as a stainless steel hypo tube. The core sleeve portion 30 can have both an exterior insulative coating 32 and an interior insulative coating, described in greater detail below.

In one embodiment as shown in FIGS. 10-11, the bone fill system 10A has a container of fill material source 2 that can be pressurized by a hydraulic source acting on a floating piston 33 (phantom view) in the syringe-like source 2 that can carry the fill material. As illustrated in the embodiments of FIGS. 10-11, it can be seen that introducer sleeve 20 has a proximal portion 35a larger in cross-section than distal portion 35b with corresponding larger and smaller interior channel portions therein. This can allow for lesser injection pressures since the cement flow needs to travel less distance through the smallest diameter distal portion of the introducer sleeve. The distal portion 35b of the introducer can have a cross section ranging between about 2 mm and 4 mm with a length ranging between about 40 mm and 60 mm. The proximal portion 35a of introducer sleeve 20 can have a cross section ranging between about 5 mm and 15 mm, or between about 6 mm and 12 mm.

Now referring to FIGS. 12 and 13, an alternative system 10B can include a bone cement injector 5 similar to the injector of FIGS. 10-11, but with an additional electrical energy delivery system for applying energy to fill material for altering its viscosity. A change in impedance compared to a data library, etc. can signal a flow change to the operator and/or the controller 45 which can automatically terminate the activation of pressure source 4.

In the system of FIGS. 12 and 13, the bone fill injection system can further include a thermal energy emitter 122' within interior channel 12 of the introducer 20 for heating a flow of bone cement from an open termination 25 in the introducer. In one embodiment, the thermal energy emitter can be within a distal portion of interior channel 12. In one embodiment, the thermal energy emitter can be a resistive heating element 122' configured to elevate the temperature of cement 14 to at least 50° C., at least 60° C., at least 70° C. or at least 80° C. The resistive element 122' can be coupled to emitter electrical source 140 as depicted in FIGS. 12 and 13 together with controller 145 that can control cement inflow parameters such as variable flow rates, constant flow rates and/or pulsed flows in combination with controlled energy delivery. The thermal energy delivery can be adapted to accelerate polymerization and increase the viscosity of a PMMA or similar bone cement as disclosed in the co-pending U.S. Patent Applications listed below. In another embodiment, the thermal energy emitter also can be an Rf emitter adapted for ohmically heating a bone cement that carries electrically conductive compositions as disclosed in the below co-pending U.S. patent applications Ser. No. 11/165,652 filed Jun. 24, 2005; Ser. No. 11/165,651 filed Jun. 24, 2005; Ser. No. 11/208,448 filed Aug. 20, 2005; and Ser. No. 11/209,035 filed Aug. 22, 2005. In another embodiment, the thermal energy emitter can be configured for delivering thermal energy to bone cement can be selected from the group consisting of a resistively heated emitter, a light energy emitter, an inductive heating emitter, an ultrasound source, a microwave emitter and any other electromagnetic energy emitter to cooperate with the bone cement. The controller 145 can be adapted to control all parameters of (i) heating the bone cement, (ii) the cement injection pressure and/or flow rate, (iii) energy delivery to cement flows in or proximate the distal end of the introducer and (iv) energy delivery to sense retrograde flows about the exterior surface of the introducer.

In one embodiment depicted in FIG. 13, the resistive heating element 122' can be a helically wound coil of a resistive material in interior bore 12 of the introducer 20. The heating element 122' can optionally be further formed from, or coated with, a positive temperature coefficient material and coupled to a suitable voltage source to provide a constant temperature heater as is known in the art. As can be seen in FIG. 13, the heating element 122' can be carried within insulative coating 232 in the interior of core sleeve 30 which can be a conductive metal as described above.

Another aspect of the invention can be understood from FIG. 13, where it can be seen that the exterior surface of sleeve 20 can have an insulative, scratch-resistant coating 32 that can comprise a thin layer of an insulative amorphous diamond-like carbon (DLC) or a diamond-like nanocomposite (DCN). It has been found that such coatings have high scratch resistance, as well as lubricious and non-stick characteristics that are useful in bone cement injectors of the invention. Such coatings are particularly useful for an introducer sleeve 20 configured for carrying electrical current for (i) impedance sensing purposes; (ii) for energy delivery to bone fill material; and/or (iii) ohmic heating of tissue. For example, when inserting a bone cement injector through the cortical bone surface of a pedicle and then into the interior of a vertebra, it is important that the exterior insulative coating portions do not fracture, chip or scratch to thereby insure that the electrical current carrying functions of the injector are not compromised.

Amorphous diamond-like carbon coatings and diamond-like nanocomposites are available from Bekaert Progressive Composites Corporations, 2455 Ash Street, Vista, Calif. 92081 or its parent company or affiliates. Further information on coatings can be found at: http://www.bekaert.com/bac/Products/Diamondlike%20-coatings.htm, the contents of which are incorporated herein by reference. The diamond-like coatings can comprise amorphous carbon-based coatings with high hardness and low coefficient of friction. The amorphous carbon coatings can exhibit non-stick characteristics and excellent wear resistance. The coatings can be thin, chemically inert and can have a very low surface roughness. In one embodiment, the coatings can have a thickness ranging between 0.001 mm and 0.010 mm; or between 0.002 mm and 0.005 mm. The diamond-like carbon coatings can be a composite of sp2 and sp3 bonded carbon atoms with a hydrogen concentration between 0 and 80%. Another diamond-like nanocomposite coating (a-C:H/a-Si:O; DLN) is made by Bakaert and is suitable for use in the bone cement injector of the invention. Some of the disclosed materials and coatings are known by the names DYLYN®PLUS, DYLYN®/DLC and CAVIDUR®.

FIG. 13 further illustrates another aspect of bone cement injector 5 that again relates to the thermal energy emitter (resistive heater 122') within interior passageway 12 of introducer 20. In one embodiment, it has been found that it can be advantageous to provide a lubricious surface layer 240 within the interior of resistive heater 122' to insure uninterrupted cements flows through the thermal emitter without sticking. In one embodiment, surface layer 240 can be a fluorinated polymer such as TEFLON® or polytetrafluroethylene (PTFE). Other suitable fluoropolymer resins can be used such as FEP and PFA. Other materials also can be used such as FEP (Fluorinated ethylenepropylene), ECTFE (Ethylenechlorotrifluoro-ethylene), ETFE, Polyethylene, Polyamide, PVDF, Polyvinyl chloride and silicone. The scope of the invention can include providing a bone cement injector having a flow channel extending therethrough with at least one open termination 25, wherein a surface layer 240 within the flow channel has a static coefficient of friction of less than 0.5, less than 0.2, or less than 0.1. In another embodiment, the emitter 122 of FIGS. 1-3 made of a PTCR material can also have a lubricious surface layer 240 of any of the polymer materials described above.

In another embodiment, the bone cement injector has a flow channel 12 extending therethrough with at least one open termination 25, wherein at least a portion of the surface layer 240 of the flow channel can be ultrahydrophobic or hydrophobic which may better prevent a hydrophilic cement from sticking.

In another embodiment, the bone cement injector can have a flow channel 12 extending therethrough with at least one open termination 25, wherein at least a portion of the surface layer 240 of the flow channel can be hydrophilic for which may prevent a hydrophobic cement from sticking.

In another embodiment, the bone cement injector can have a flow channel 12 extending therethrough with at least one open termination in a distal end thereof, wherein the surface layer 240 of the flow channel can have high dielectric strength, a low dissipation factor, and/or a high surface resistivity.

In another embodiment, the bone cement injector can have a flow channel 12 extending therethrough with at least one open termination 25 in a distal end thereof, wherein the surface layer 240 of the flow channel can be oleophobic. In another embodiment, the bone cement injector can have a flow channel 12 extending therethrough with at least one open termination 25 in a distal end thereof, wherein the surface layer 240 of the flow channel can have a substantially low coefficient of friction polymer or ceramic.

In another embodiment, the bone cement injector can have a flow channel 12 extending therethrough with at least one open termination 25 in a distal end thereof, wherein the surface layer 240 of the flow channel can have a wetting contact angle greater than 70°, greater than 85°, and greater than 100°.

In another embodiment, the bone cement injector can have a flow channel 12 extending therethrough with at least one open termination in a distal end thereof, wherein the surface layer 240 of the flow channel can have an adhesive energy of less than 100 dynes/cm, less than 75 dynes/cm, and less than 50 dynes/cm.

The apparatus above also can be configured with any other form of thermal energy emitter that includes the non-stick and/or lubricious surface layer as described above. In one embodiment, the thermal energy emitter can comprise at least in part an electrically conductive polymeric layer. In one such embodiment, the electrically conductive polymeric layer can have a positive temperature coefficient of resistance.

Figure 14:
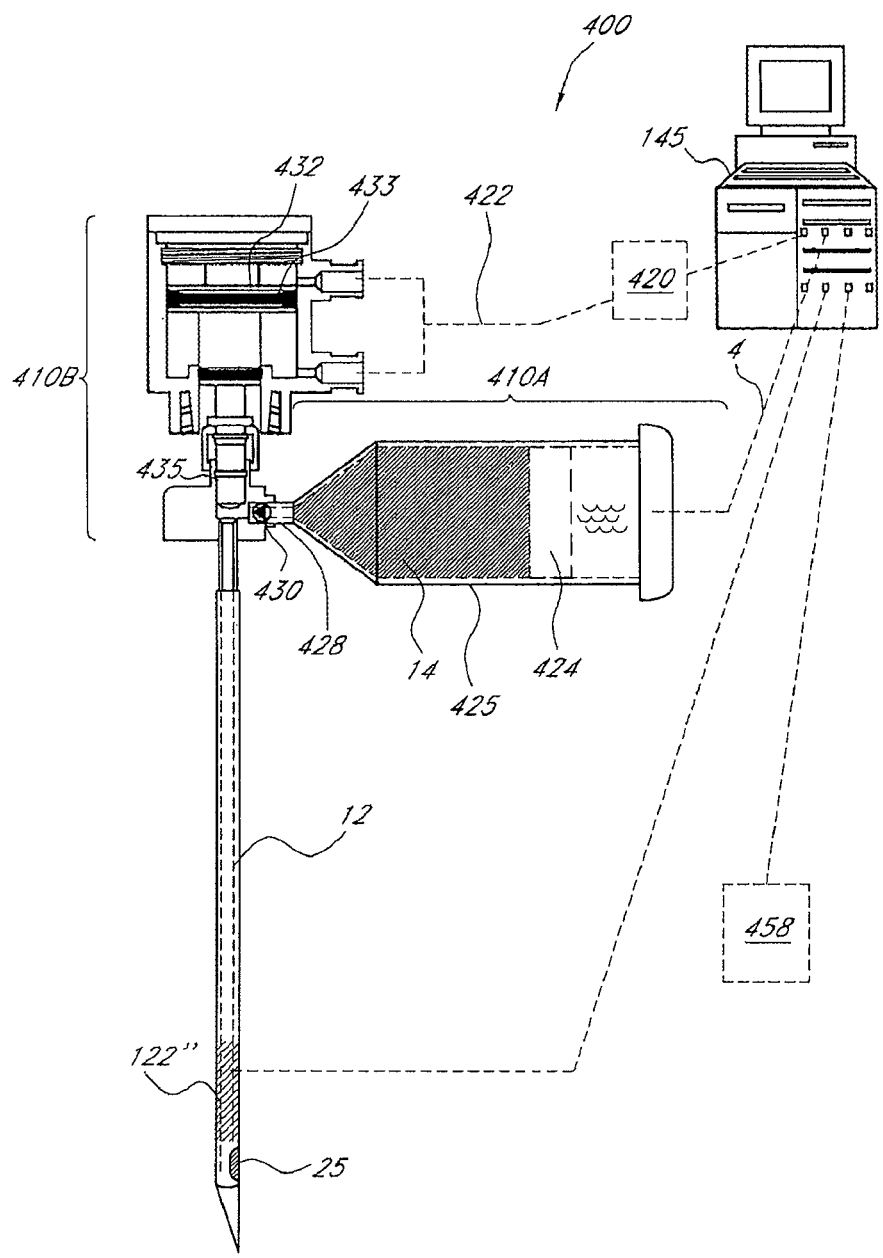
FIG. 14 is a schematic view of another embodiment of an injection system for delivering bone fill material into a bone.

FIG. 14 is an illustration of an alternative bone cement injector system 400 with a flow channel 12 extending therethrough. The cement injector 400 can be coupled to both a low pressure source 410A and a high pressure source 410B that can move cement from reservoir or fill source 425 into and through the injector. The low pressure source 410A can be similar to that described in the embodiment of FIG. 10, wherein a fluid hydraulic source can be coupled to remote driver or pressurizing source in the controller indicated at 145. It can be understood that this low pressure source can apply pressure on floating piston 424 to move cement or fill material 14 through reservoir body 425 to a distal channel 428 that can carry a one-way valve 430.

In the illustrated embodiment of FIG. 14, the high pressure source 410B is a mechanical pump mechanism comprising a piston pump with a back-and-forth stroke, which is actuated by a pneumatic pressure source 420 and conduit 422 that is controlled by controller 145. In FIG. 14, it can be seen that piston 432 with an o-ring 433 can be actuated within a bore with a pump shaft 435 extending into bore or channel 12 of the injector. The pneumatic source pumps and extracts air or another gas from opposing sides of piston 432 in sequence to reciprocate the piston a fixed distance. It can be understood that the backstroke of piston 432 can draw a predetermined volume of cement thru one-way valve 430 into channel 12. Then, a forward stroke of piston 432 and pump shaft 435 can drive the predetermined volume of cement under very high pressure through the channel 12 in the injector to exit from port 25 into a targeted site in bone. At the same time, the high pressure source 410B and its actuation can provide signals of the flow rate to controller 145 that in turn can be processed with algorithms to modulate operational parameters such as energy delivery and flow rate.

In the embodiment of FIG. 14, it can be understood that the low pressure source 410A operating in conjunction with the high pressure source 410B can provide a precise flow rate of fill material or cement 14 through channel 12 in the injector which can then further allow a selected level of energy to be applied to the cement flow from a heat emitter or element 122" in channel 12. In the injector system 400 of FIG. 14, the heating element 122" can be any type of resistive heat emitter, laser emitter, a light channel, an electrode, an antenna, Rf or microwave emitter, ultrasound emitter or the like. In one embodiment, the heat emitter 122" can be a tubular member of a PTCR or NTCR material (positive temperature coefficient of resistance or negative temperature coefficient of resistance). Similar to some of the previously discussed embodiments, the embodiment of FIG. 14 can, in one embodiment, also include the polymer PTCR heat emitter 122" illustrated in FIG. 3.

In the embodiment of FIG. 14, one advantage of the combination or the low pressure source 410A and the high pressure source 410B is that the high pressure source located in the handle end of the injector body can ensure that there is no issue of compliance in components downstream from the high pressure piston pump mechanism. As can be understood from FIG. 14, the pumping rate of the high pressure source 410B can be controlled and known by the controller 145 which can then allow for (i) modulation of the flow rate in relation to energy delivery, (ii) or the modulation of energy delivery in relation to flow rate, or (iii) both. In the embodiment of FIG. 10, the pump mechanism that generated the cement flow can be located at the controller remote from the injector body which can allow for some compliance in the hydraulic system components downstream from the pump mechanism, which can result in slight uncertainty as to the precise flow rate through the heat emitter 122". It has been found that precision in flow rate sensing is important in determining the proper energy dosing to provide the optimal bone cement viscosity and temperature in the injector and at the flow outlet 25 of the injector.

Figure 15:
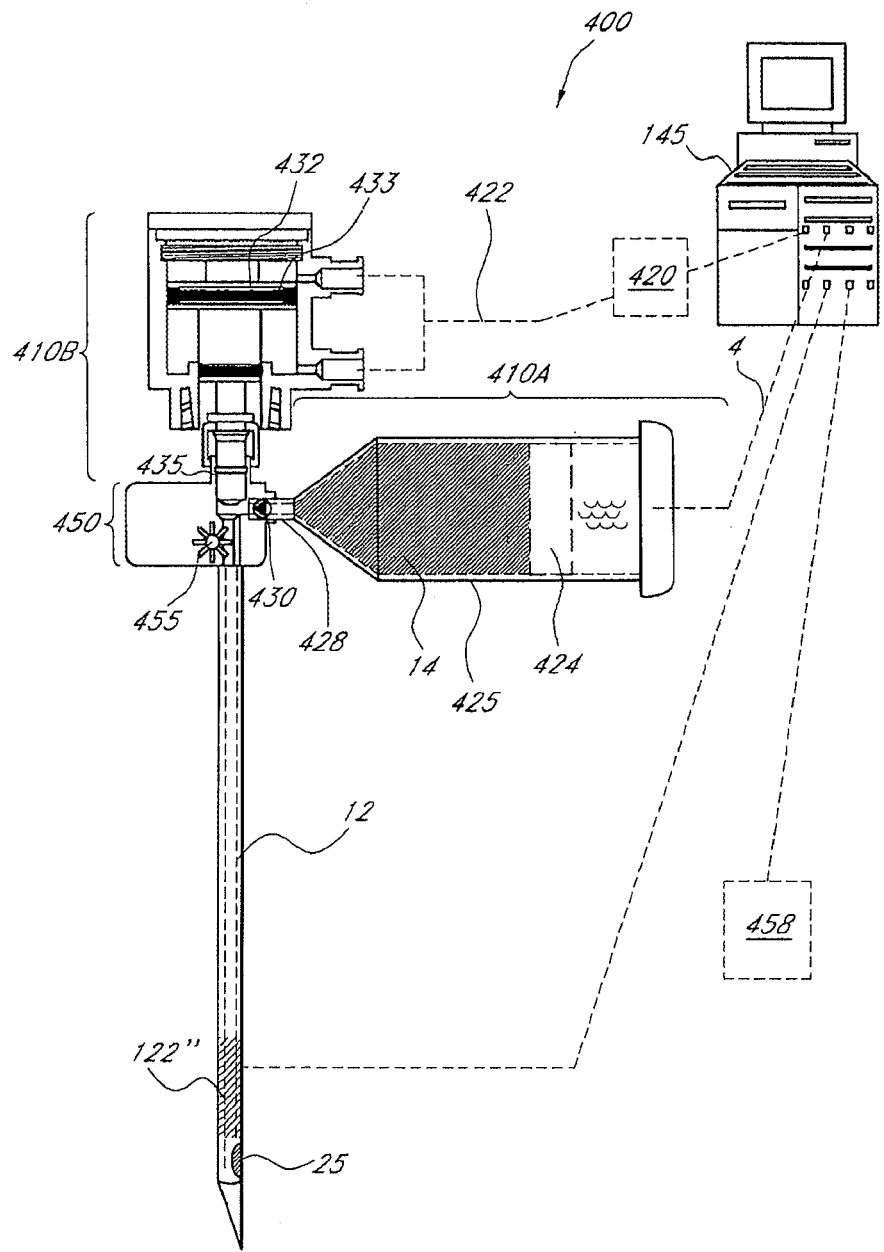
FIG. 15 is a schematic view of another embodiment of an injection system for delivering bone fill material into a bone, similar to that of FIG. 14.

In another aspect of the invention referring to FIGS. 14 and 15, the bone cement injection system 400 can include a bone cement injector body with a flow channel 12 extending therethrough from a proximal handle end though a medial portion to a distal end portion having a flow outlet 25, a bone cement source having a flow channel in communication with the flow channel in the injector body, and a one-way valve 430 in the flow channel of either the injector body or cement source. The one-way valve can be in the proximal handle end of the injector body, in a medial portion of the injector body or in a flow channel portion of the cement source. The one-way valve can be any flexible polymer such as silicone and comprise a duck-bill valve or the one-way valve can be a flap-valve.

With reference to FIGS. 10 and 14, a method of performing bone cement injection in an osteoplasty can comprise (i) providing a bone cement injector body carrying a flow control mechanism such as a pump capable of generating flow rate signals of cement flow caused by the mechanism, (ii) causing cement flow through the injector body, and (iii) applying thermal energy from an emitter in the injector body to the cement flow wherein a controller modulates the application of thermal energy in response to flow rate signals. In such embodiments, the controller can comprise a computer control mechanism. In the embodiment of FIG. 14, the flow control mechanism can include at least one reciprocating piston. In embodiments similar to FIG. 14, it can be easily understood that other types of flow control mechanisms in the bone cement injector body or handle can be used, such as a peristaltic pump mechanism, a diaphragm pump mechanism, rotary vane pump mechanism, a screw pump mechanism and the like. In this method of the invention, the flow control mechanism that generates flow rate signals can be unitary with the flow driver mechanism.

With reference to FIG. 15, the apparatus and method of one embodiment of the invention can further include providing a flow meter device 450 in the handle of the cement injector that can optionally be independent of the pressure mechanism that drives the cement flow. In FIG. 15, a flow control mechanism or flow sensing mechanism can comprise an impeller flowmeter 455, but other types of flow control mechanisms or meters can be suitable and can be selected from the group of gear flowmeters, positive displacement flowmeters, oval gear flowmeters, sliding vane flowmeters, nutating disc flowmeters, oscillating piston flowmeters, helical screw flowmeters, Pelton wheel flowmeters, ultrasonic flowmeters, and thermal mass flow meters.

Another method of performing bone cement injection in a vertebroplasty can comprise providing a bone cement injector body carrying a flow control mechanism capable of providing flow rate signals of cement flows therein, actuating a flow drive mechanism thereby causing cement flows within a passageway in the injector body, applying energy to the cement flow from an emitter in the injector body wherein a controller can modulate the application of said energy in response to said flow rate signals, wherein the flow control mechanism and flow drive mechanism can be independent.

The method of performing bone cement injections can include providing continuous cement flows, pulsed cement flows or cement flows in intervals.

The method of performing bone cement injections can include providing a flow drive mechanism and controller capable of providing cement flows ranging from 0.1 cc/min to 10.0 cc/min, or from 1.0 cc/min to 5.0 cc/min.

Another method of performing bone cement injection can include providing a bone cement injector system having a first low pressure system for moving cement from a first chamber to a second chamber, and second high pressure system for moving cement from the second chamber through an extending member for introduction into a bone using a pressure of less than about 10 psi to move cement from the first chamber to the second chamber, and using a pressure of greater than about 20 psi to move cement from the second chamber through the extending member into bone.

In accordance with another embodiment, an apparatus for bone cement injection is provided that can include an injector body having a handle portion and an extension portion that can be configured for insertion into cancellous bone, a member having a first chamber carrying fill material coupleable to a second chamber in said injector body, a first low pressure drive mechanism operatively coupled to the first chamber for moving fill material from said first chamber to said second chamber; and a second high pressure drive mechanism operatively coupled to the second chamber for moving fill material from said second chamber through said extension portion and into cancellous bone. In this embodiment, the first low pressure drive mechanism can operate using a pressure of less than about 10 psi. The second high pressure drive mechanism can operate using a pressure of greater than about 20 psi.

With reference to FIGS. 14 and 15, an apparatus for bone cement injection is provided that can include an injector body 400 having a handle portion and an extension portion configured for at least partial insertion into cancellous bone, at least one drive mechanism operatively coupled to a chamber within or coupleable to the injector body for moving fill material from said chamber through said extension portion and into cancellous bone, a power or pressure source flexibly coupled to said drive mechanism, and a remote hand-held switch mechanism 458 operatively coupled to the power source or controller 145. The hand-held switch mechanism 458 can be an on-off or rheostat-type switch for variably actuating cement flows, and/or a switch mechanism is capable actuating a thermal energy emitter. Of particular interest, the hand-held switch mechanism 458 can be remote and not attached to the cement injector itself, thus allowing the physician to stand far from an X-ray source and wherein the cable extending to the switch is not linked to the injector which can tend to move to rotate the injector.

In accordance with another embodiment, a method for bone cement injection in an osteoplasty procedure comprise (a) providing a bone cement injector body carrying a PTCR or NTCR material (positive temperature coefficient of resistance or negative temperature coefficient of resistance); (b) causing cement flow through the injector body; and (c) measuring an electrical parameter of the a PTCR or NTCR material in response to heat transfer from the cement flow to the PTCR or NTCR material to thereby determine a selected parameter of the cement flow. It has been found that the change in impedance of the temperature coefficient material can be used to accurately determine the flow rate of the cement flow. In turn, the signals can indicate a measurement of impedance, capacitance, a change in impedance over an interval, or the rate of change of impedance of the temperature coefficient material to determine the viscosity of the cement within the cement flow proximate to the PTCR material or at the flow outlet.

Another method of bone cement injection can include modulating the rate of cement flow in response to determining a selected parameter of the cement flow such as flow rate. The method of bone cement injection can further include applying and modulating thermal energy application from an emitter in the injector body to the cement flow. The method of bone cement injection can further include modulating the application of energy in response to signals that relate to a selected parameter such as flow rate of the cement flow.

Another method of bone cement injection comprises (a) providing a bone cement injector body carrying a PTCR (positive temperature coefficient of resistance) material in a flow channel therein, (b) applying a selected level of energy to a cement flow through the PTCR material, and (c) utilizing an algorithm that processes impedance values of the PTCR material to determine the cement flow rate. The method of bone cement injection further includes modulating a cement injection parameter in response to the processed impedance values.

Still another method of bone cement injection comprises (a) providing a bone cement injector body carrying a PTCR material or other thermal energy emitter in a flow channel therein, (b) causing a selected cement flow rate and a selected level of energy delivery to the cement flow through the emitter, and (c) modulating the selected flow rate and/or energy delivery to maintain a substantially constant impedance value of the emitter material over a cement injection interval. The selected cement injection interval can be at least 1 minute, at least 5 minutes, at least 10 minutes and at least 15 minutes. In another aspect of the invention, the method modulated the selected flow rate and/or energy delivery to maintain a substantially constant viscosity of bone cement ejected from the injector over a cement injection interval. The system and energy source is configured for applying energy of at least 0.01 Watt, 0.05 Watt, 0.10 Watt, 0.50 Watt and 1.0 Watt. In another aspect, the energy source and controller are configured for accelerating polymerization rate of the bone cement to a selected endpoint in less than 1 second, 5 seconds, 10 seconds, 20 seconds, 30 seconds, 45 seconds, 60 seconds and 2 minutes.

Another method of bone cement injection utilizes apparatus as described above and comprises (a) providing a bone cement injector body with a flow channel extending therethrough from a proximal handle end though a medial portion to a distal end portion having a flow outlet, (b) causing cement flow through the flow channel, and (c) warming the cement flow with an energy emitter in a proximal end or medial portion thereof to initiate or accelerate polymerization of the cement of the cement flow. The method includes providing a flow rate of the cement flow that ranges from 0.1 cc/minute to 20 cc/minute, from 0.2 cc/minute to 10 cc/minute, and from 0.5 cc/minute to 5 cc/minute.

The above-described method of bone cement injection allows a predetermined cement flow rate to provide a selected interval in which the cement flows is allowed to polymerize in the flow channel downstream from the energy emitter. This method includes providing a selected interval of greater than 1 second, greater than 5 seconds, greater than 10 seconds, greater than 20 seconds, and greater than 60 seconds.

The above-described method utilizes an energy emitter that applies energy sufficient to elevate the temperature of the bone cement by at least 1° C., at least 2° C., and at least 5° C. The method of bone cement injection includes utilizing an energy emitter that applies at least 0.1 Watt of energy to the cement flow, at least 0.5 Watt of energy to the cement flow, and at least 1.0 Watt of energy to the cement flow. The method includes the flow rate of the cement flow being adjusted in intervals by controller 145, or being continuously adjusted by a controller.

With reference to FIGS. 14 and 15, the bone cement injection system can include a bone cement injector body with a flow channel extending therethrough from a proximal handle end though a medial portion to a distal end portion having a flow outlet, a bone cement source having a flow channel in communication with the flow channel in the injector body, and a one-way valve 430 in the flow channel of either the injector body or the cement source. The one-way valve can be in the proximal handle end of the injector body, in a medial portion of the injector body or in a flow channel portion of the cement source. The one-way valve can be any flexible polymer such as silicone and comprise a duck-bill valve or the one-way valve can be a flap-valve.

Figure 16:
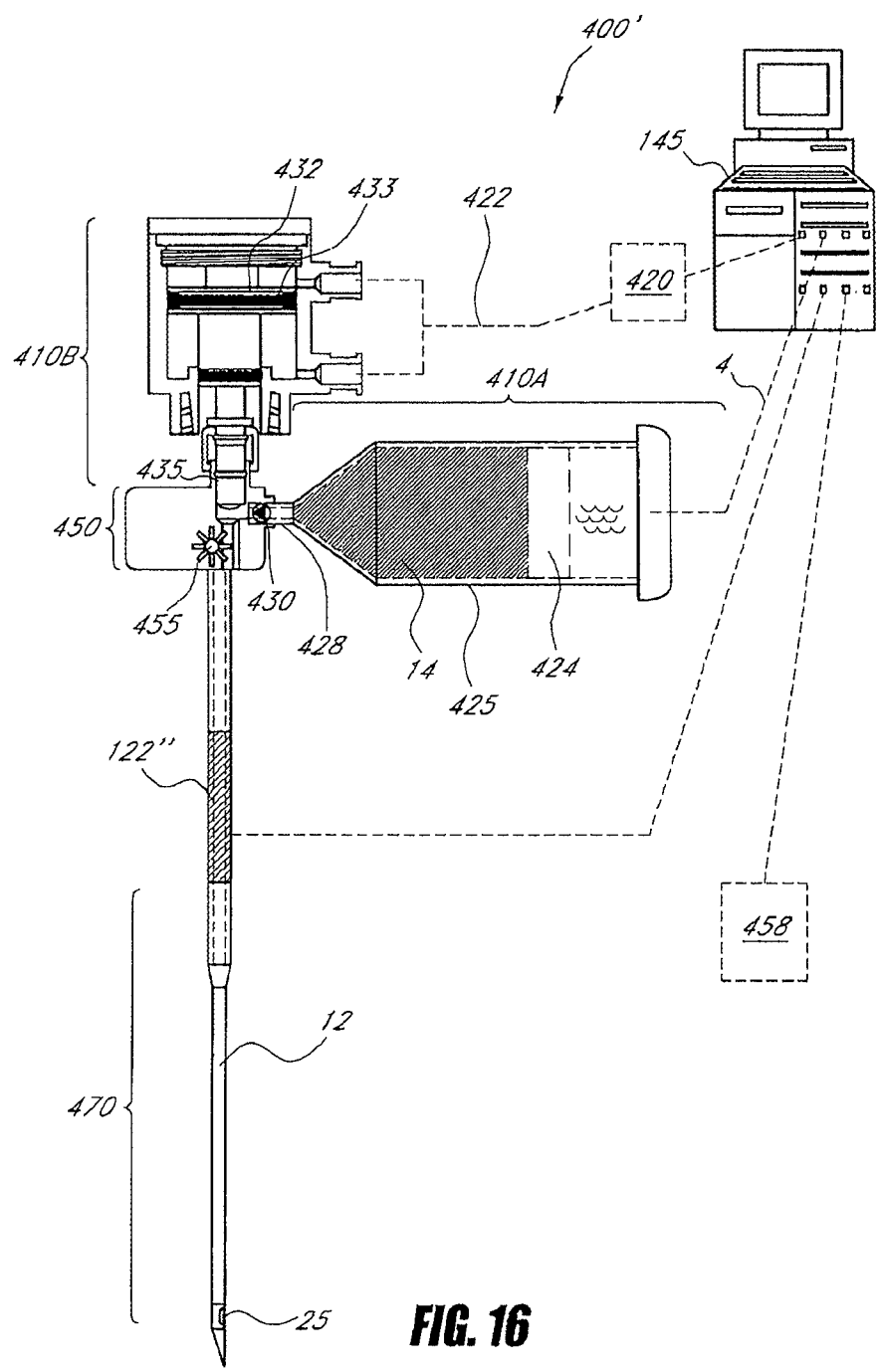
FIG. 16 is a schematic view of another embodiment of an injection system for delivering bone fill material into a bone, similar to that of FIGS. 14 and 15.

In one embodiment of bone cement injection system referring to FIG. 16, the bone cement injector body 400' can have a flow channel 12 extending therethrough from a proximal handle end though a medial portion to a distal end portion having a flow outlet 25; and a heating element 122" in the proximal handle end or the medial portion of the injector body that is a selected axial extension dimension 470 from the flow outlet 25. In one embodiment, the heating element 122" can be at least 5 mm proximal from the flow outlet 25, at least 10 mm proximal from the flow outlet 25, or at least 20 mm proximal from the flow outlet 25. The flow rate of the cement can be controlled by the controller so that over the extension dimension 470, the cement can undergo a predetermined degree of polymerization due to exothermic heating and due to the acceleration of polymerization caused by the warming of the cement flow.

In another embodiment, the bone cement injection system can include a bone cement injector body with a flow channel extending therethrough from a proximal handle end though a medial portion to a distal end portion having a flow outlet, a heating element in a proximal handle end or medial portion of the injector body; and a controller system for controlling operational parameter of the system, wherein control algorithms can include algorithms that plot the time of initial mixing of the bone cement, algorithms that plot cement viscosity in relationship to said time of initial mixing, and algorithms that plot cement viscosity in relation to a temperature profile of the cement. The controller and algorithms can be capable of modulating flow rate and energy application to provide a substantially constant cement viscosity at the flow outlet.

In another embodiment, the power delivery can be accomplished from a battery system rather that an RF generator as shown in FIGS. 14 and 15. It has been found that power delivery requirements for warming the cement in the handle end of the injector or the medial portion of the injector can be quite low, thus any form of battery can be adapted to warm the heater and the cement flow.

A method of altering a fill material can include at least one of a radiofrequency source, a laser or light source, a microwave source, a magnetic source and an ultrasound source. Each of these energy sources can be configured to preferentially deliver energy to a cooperating, energy sensitive filler component carried by the fill material. For example, such filler can be suitable chromophores for cooperating with a light source, ferromagnetic materials for cooperating with magnetic inductive heating means, or fluids that thermally respond to microwave energy. In other embodiments the system of the invention can use any suitable energy source to accomplish the purpose of altering the viscosity of the fill material 14.

The above description of the invention is intended to be illustrative and not exhaustive. Particular characteristics, features, dimensions and the like that are presented in dependent claims can be combined and fall within the scope of the invention. The invention also encompasses embodiments as if dependent claims were alternatively written in a multiple dependent claim format with reference to other independent claims. Specific characteristics and features of the invention and its method are described in relation to some figures and not in others, and this is for convenience only. While the principles of the invention have been made clear in the descriptions and combinations, it will be obvious to those skilled in the art that modifications may be utilized in the practice of the invention, and otherwise, which are particularly adapted to specific environments and operative requirements without departing from the principles of the invention. The appended claims are intended to cover and embrace any and all such modifications, with the limits only of the true purview, spirit and scope of the invention.

Certain embodiments of the invention provide bone cement injectors and control systems that allow for vertebroplasty procedures that inject cement having a substantially constant viscosity over an extended cement injection interval.

In certain embodiments, a computer controller is provided to control cement flow parameters in the injector and energy delivery parameters for selectively accelerating polymerization of bone cement before the cement contacts the patient's body.

Of course, the foregoing description is that of certain features, aspects and advantages of the present invention, to which various changes and modifications can be made without departing from the spirit and scope of the present invention. Moreover, the bone treatment systems and methods need not feature all of the objects, advantages, features and aspects discussed above. Thus, for example, those skill in the art will recognize that the invention can be embodied or carried out in a manner that achieves or optimizes one advantage or a group of advantages as taught herein without necessarily achieving other objects or advantages as may be taught or suggested herein. In addition, while a number of variations of the invention have been shown and described in detail, other modifications and methods of use, which are within the scope of this invention, will be readily apparent to those of skill in the art based upon this disclosure. It is contemplated that various combinations or subcombinations of these specific features and aspects of embodiments may be made and still fall within the scope of the invention. Accordingly, it should be understood that various features and aspects of the disclosed embodiments can be combined with or substituted for one another in order to form varying modes of the discussed bone treatment systems and methods.

What is claimed is:

1. A method for treating a bone, comprising:
   mixing two-components to form bone cement within a syringe body, the syringe body forming part of a source of bone cement;
   inserting at least a portion of an elongated bone cement injector percutaneously through a patient's skin into a cancellous bone portion of a bone;
   coupling a proximal end of the injector to an outlet of a handle body;
   coupling the source of bone cement to an inlet of the handle body;
   coupling a first side of a two-sided plunger with the syringe body;
   flowing bone cement from the source of bone cement through the handle body and through a bore in the injector into the cancellous bone by hydraulically advancing a second side of the two-sided plunger and thereby advancing the first side of the two-sided plunger within the syringe body; and
   applying energy to the bone cement as it flows through the handle body in an amount sufficient to accelerate a setting rate in the bone cement to increase the viscosity of the bone cement so as to reach a selected polymerization endpoint as the bone cement exits the injector and prior to introduction of the bone cement into bone.

2. The method of claim 1, wherein the injector couples to the handle body at a location outside of the patient.

3. The method of claim 1, wherein the selected polymerization endpoint provides a bone cement viscosity that substantially inhibits extravasation of bone cement upon introduction of the bone cement into the bone.

4. The method of claim 1, wherein the applied energy accelerates the setting rate by at least 20%.

5. The method of claim 1, wherein the applied energy accelerates the setting rate by at least 60%.

6. The method of claim 1, further comprising modulating the applied energy via a controller based at least in part on a signal indicative of a temperature of the bone cement that is communicated to the controller.

7. The method of claim 1, further comprising modulating the applied energy via a controller based at least in part on a signal indicative of a flow rate of the bone cement that is communicated to the controller.

8. The method of claim 1, further comprising modulating a rate of flow of the bone cement via a controller.

9. The method of claim 1, wherein applying energy includes delivering energy from an energy source comprising at least one of a radiofrequency source, a resistive heat source, an electrical source, a PTCR constant temperature heat source, a non-coherent light source, a laser source, an LED source, a microwave source, a magnetic source and an ultrasound source.

10. The method of claim 1, further comprising activating the flow of bone cement into the cancellous bone wherein the step of activating can be performed outside of a radiation field created by an imaging system used while treating the bone.

11. The method of claim 1, further comprising controlling the application of energy from an energy source with a computer controller.

12. The method of claim 11, wherein controlling the application of energy from the energy source further comprises controlling the application of energy from the energy source to achieve a generally constant bone cement viscosity at an outlet opening in the bore of the injector.

13. The method of claim 1, wherein applying energy to the bone cement comprises applying energy to the bone cement via a thermal energy emitter disposed in the handle body, the thermal energy emitter comprising a polymeric positive temperature coefficient of resistance (PTCR) material and having spaced apart electrodes on a surface of the thermal energy emitter.

14. The method of claim 13, wherein the electrodes are spaced apart so as to generate substantially uniform heating of the thermal energy emitter along its length.

15. The method of claim 1, wherein applying energy to the bone cement as it flows through the handle body comprises applying energy with a thermal energy emitter surrounding a flow channel in the handle body.

16. The method of claim 15, wherein a lubricious surface layer defines the flow channel in the handle body at the thermal energy emitter.

17. A method of bone cement delivery, comprising:
mixing components of a bone cement to begin polymerization of the bone cement within a bone cement container;
coupling an elongated bone cement injector to an outlet of a handle body, the handle body defining a flow channel extending therethrough from an inlet of the handle body to the outlet of the handle body;
coupling the bone cement container to the inlet of the handle body;
flowing the mixed and polyermizing bone cement from the container into the flow channel in the handle body;
applying energy to the bone cement passing through the flow channel with a thermal energy emitter disposed about the flow channel in the handle body in order to controllably increase the viscosity of the bone cement as it flows therethrough and prior to introduction of the bone cement into bone, a lubricious surface layer defining the flow channel within an interior of the thermal energy emitter;
flowing the mixed and polyermizing bone cement from the flow channel in the handle body and through a bore in the injector into cancellous bone.

18. The method of claim 17, wherein applying energy to the bone cement further comprises applying energy to accelerate a setting rate of the bone cement so as to reach a selected polymerization endpoint as the bone cement exits the injector.

19. The method of claim 17, further comprising controlling the application of energy from an energy source with a computer controller.

20. The method of claim 19, wherein controlling the application of energy from the energy source further comprises controlling the application of energy from the energy source to achieve a generally constant bone cement viscosity at an outlet opening in the bore of the injector.

21. The method of claim 19, further comprising accelerating a polymerization rate of the bone cement by at least 20%.

22. The method of claim 19, further comprising accelerating a polymerization rate of the bone cement by at least 60%.

23. The method of claim 17, further comprising depressing an activation switch to initiate flowing the mixed and polyermizing bone cement from the flow channel in the handle body and through a bore in the injector into the cancellous bone.

24. The method of claim 23, wherein the activation switch is located remotely from the handle body, the injector and the container.

25. The method of claim 17, wherein the thermal energy emitter comprises at least one of a resistive heater, a PTCR constant temperature heater, a fiber optic emitter, a light channel, an LED emitter, an ultrasound transducer, an electrode and an antenna.

26. The method of claim 17, wherein the thermal energy emitter comprises a polymeric positive temperature coefficient of resistance (PTCR) material and has spaced apart electrodes on a surface of the thermal energy emitter.

27. The method of claim 26, wherein the electrodes are spaced apart so as to generate substantially uniform heating of the thermal energy emitter along its length.

28. The method of claim 17, further comprising coupling a first side of a two-sided plunger with the bone cement container.

29. The method of claim 28, wherein flowing the mixed and polyermizing bone cement from the container into the flow channel in the handle body comprises hydraulically advancing a second side of the two-sided plunger and thereby advancing the first side of the two-sided plunger within the bone cement container.

* * * * *

UNITED STATES PATENT AND TRADEMARK OFFICE
CERTIFICATE OF CORRECTION

PATENT NO. : 8,556,910 B2  
APPLICATION NO. : 12/062345  
DATED : October 15, 2013  
INVENTOR(S) : Truckai et al.

Page 1 of 1

It is certified that error appears in the above-identified patent and that said Letters Patent is hereby corrected as shown below:

In the Specification

Column 3 at line 44, After "pressures" insert --(e.g., up to 200 or 300 psi) to inflate the balloon which crushes and compacts cancellous bone. Expansion of the balloon under high pressures close to cortical bone can fracture the cortical bone, typically the endplates, which can cause regional damage to the cortical bone with the risk of cortical bone necrosis. Such cortical bone damage is highly undesirable as the endplate and adjacent structures provide nutrients for the disc.--.

Column 9 at line 22, delete "thereof'" and insert --thereof.--.

Column 10 at line 58, delete "that" and insert --than--.

Column 15 at line 42, delete "Bakaert" and insert --Bekaert--.

Column 15 at line 54, delete "polytetrafluroethylene" and insert --polytetrafluoroethylene--.

Column 19 at line 29, delete "the a" and insert --the--.

In the Claims

Column 23 at line 49, Claim 17, delete "polyermizing" and insert --polymerizing--.

Column 24 at line 6, Claim 17, delete "polyermizing" and insert --polymerizing--.

Column 24 at lines 26-27, Claim 23, delete "polyermizing" and insert --polymerizing--.

Column 24 at line 48, Claim 29, delete "polyermizing" and insert --polymerizing--.

Signed and Sealed this  
Second Day of September, 2014

Michelle K. Lee  
*Deputy Director of the United States Patent and Trademark Office*